US007049081B2

(12) United States Patent
Kunsch et al.

(10) Patent No.: US 7,049,081 B2
(45) Date of Patent: May 23, 2006

(54) DIAGNOSTIC METHODS BASED ON HUMAN BTG-2 AND BTG-3 POLYPEPTIDES

(75) Inventors: Charles A. Kunsch, Norcross, GA (US); Arvind Chopra, Gaithersburg, MD (US); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 10/739,043

(22) Filed: Dec. 19, 2003

(65) Prior Publication Data

US 2004/0131597 A1    Jul. 8, 2004

Related U.S. Application Data

(60) Division of application No. 09/843,846, filed on Apr. 30, 2001, now Pat. No. 6,689,360, which is a division of application No. 09/221,844, filed on Dec. 29, 1998, now Pat. No. 6,258,777, which is a division of application No. 08/718,738, filed on Sep. 18, 1996, now Pat. No. 6,013,469, which is a continuation-in-part of application No. 08/463,382, filed on Jun. 5, 1995, now abandoned, and a continuation-in-part of application No. 08/460,104, filed on Jun. 2, 1995, now abandoned, said application No. 08/463,382 and application No. 08/460,104, is a continuation-in-part of application No. PCT/US95/03323, filed on Mar. 17, 1995.

(51) Int. Cl.
  *G01N 33/53*   (2006.01)
  *C07K 14/00*   (2006.01)
  *A61K 38/17*   (2006.01)
(52) U.S. Cl. .................... 435/7.1; 514/21; 530/350; 436/501
(58) Field of Classification Search ................ 436/501; 514/21; 530/350
  See application file for complete search history.

(56) References Cited

U.S. PATENT DOCUMENTS 6,013,469 A * 1/2000 Kunsch et al. ............. 435/69.1

FOREIGN PATENT DOCUMENTS

WO    WO96/29401    9/1996

OTHER PUBLICATIONS

Matsuda et al., FEBS Letters, 2001, 497:67-72.*
The Merck Manual of Dignosis and Therapy, 1999, Published by Merck Research Laboratories, pp. 978-979.*
Attwood, Science 2000, vol. 290, pp. 471-473.*
Skolnick et al. Trends in Biotech. 2000, vol. 18, pp. 34-39.*
Barton, G.J., "Protein sequence alignment and database scanning," in: Protein Structure Prediction: A Practical Approach, Sternberg, M.J.E., ed., IRL Press at Oxford University Press, Oxford, U.K., pp. 31-63 (1996).
Bradbury, et al., "Molecular cloning of PC3, a putatively secreted protein whose mRNA is induced by nerve growth factor and depolarization," Proc. Natl. Acad. Sci. USA, 88:3353-3357 (1991).
Fletcher, et al., "Structure and expression of TIS21, a primary response gene induced by growth factors and tumor promoters," J. Biol. Chem., 266:14511-14518 (1991).
George, et al., "Current methods in sequence comparison and analysis," in: Macromolecular Sequencing and Synthesis Selected Methods and Applications, Schlesinger, D.H., ed., Alan R. Liss, Inc., New York, N.Y., pp. 127-149 (1988).
Guehenneux, et al., "Cloning of the mouse BTG3 gene and definition of a new gene family (the BTG Family) involved in the negative control of the cell cycle," Leukemia, 11:370-375 (Mar. 1997).
Hamil, et al., "Cloning of rat sertoli cell follicle-stimulating hormone primary response complementary deoxyribonucleic acid: Regulation of TSC-22 gene expression," Endocrinology, 134:1205-1212 (1994).
Ikematsu, et al., "Tob2, a novel anti-proliferative Tob/BTG1 family member, associates with a component of the CCR4 transcriptional regulatory complex capable of binding cyclin-dependent kinases," Oncogene, 18(52):7432-7441 (1999).
Marshall, C.J., "Tumor suppressor genes," Cell, 86:313-326 (1991).

(Continued)

*Primary Examiner*—Phillip Gambel
*Assistant Examiner*—Ilia Ouspenski
(74) *Attorney, Agent, or Firm*—Human Genome Sciences, Inc.

(57) ABSTRACT

The present invention relates to novel antiproliferative genes. More specifically, isolated nucleic acid molecules are provided encoding the human B-cell translocation genes 2 and 3 (BTG-2 and BTG-3). BTG-2 and BTG-3 polypeptides are also provided, as are vectors, host cells and recombinant methods for producing the same.

4 Claims, 6 Drawing Sheets

OTHER PUBLICATIONS

Matsuda, et al., "In search of a function for the TIS21/PC3/BTG1/TOB family," FEBS Letters, 497:67-72 (2001).

Matsuda, et al., "Tob, a novel protein that interacts with p185 (erbB2), is associated with antiproliferative activity," Oncogene, 12:705-713 (1996).

Raburn, et al., "Stage-specific expression of B cell translocation in Gene 1 in rat testis," Endocrinology, 136:5769-5777 (1995).

Rimokh, et al., "A chromosome 12 coding region is juxtaposed to the MYC protooncogene locus in a t(8;12)(q24;q22) translocation in a case of B-cell chromic leukemia," Genes Chromosom. Canc., 3:24-36 (1991).

Rouault, et al., "Sequence analysis reveals that the BTG1 anti-proliferative gene is conserved throughout evolution in its coding and 3-prime non-coding regions," Gene, 129:303-306 (1993).

Rouault, et al., "BTG1, a member of a new family of antiproliferative genes," EMBO J., 11(4):1663-1670 (1992).

Rouault, et al., "Identification of BTG2, an antiproliferative p53-dependent component of the DNA damage cellular response pathway," Nature Genet., 14:482-486 (1996).

Weinberg, R.A., "Tumor suppressor genes," Science, 254:1138-1146 (1991).

* cited by examiner

```
  1 GGCACGAGATTTTGTGGCGTAGAGCTATGCAGCTTGAAATCCAAGTAGCACTAAATTTTA
                                 M  Q  L  E  I  Q  V  A  L  N  F  I

61 TTATTTCGTATTTGTACAATAAGCTTCCCAGGAGACGTGTCAACATTTTTGGTGAAGAAC
     I  S  Y  L  Y  N  K  L  P  R  R  R  V  N  I  F  G  E  E  L

121 TTGAAAGACTTCTTAAGAAGAAATATGAAGGGCACTGGTATCCTGAAAAGCCATACAAAG
     E  R  L  L  K  K  K  Y  E  G  H  W  Y  P  E  K  P  Y  K  G

181 GATCGGGGTTTAGATGTATACACATAGGGGAGAAAGTGGACCCAGTGATTGAACAAGCAT
     S  G  F  R  C  I  H  I  G  E  K  V  D  P  V  I  E  Q  A  S

241 CCAAAGAGAGTGGTTTGGACATTGATGATGTTCGTGGCAATCTGCCACAGGATCTTAGTG
     K  E  S  G  L  D  I  D  D  V  R  G  N  L  P  Q  D  L  S  V

301 TTTGGATCGACCCATTTGAGGTTTCTTACCAAATTGGTGAAAAGGGACCAGTGAAGGTGC
     W  I  D  P  F  E  V  S  Y  Q  I  G  E  K  G  P  V  K  V  L

361 TTTACGTGGATGATAATAATGAAAATGGATGTGAGTTGGATAAGGAGATCAAAAACAGCT
     Y  V  D  D  N  N  E  N  G  C  E  L  D  K  E  I  K  N  S  F

421 TTAACCCAGAGGCCCAGGTTTTTATGCCCATAAGTGACCCAGCCTCATCAGTGTCCAGCT
     N  P  E  A  Q  V  F  M  P  I  S  D  P  A  S  S  V  S  S  S

481 CTCCATCGCCTCCTTTTGGTCACTCTGCTGCTGTAAGCCCTACCTTCATGCCCCGGTCCA
     P  S  P  P  F  G  H  S  A  A  V  S  P  T  F  M  P  R  S  T

541 CTCAGCCTTTAACCTTTACCACTGCCACTTTTGCTGCCACCAAGTTCGGCTCTACCAAAA
     Q  P  L  T  F  T  T  A  T  F  A  A  T  K  F  G  S  T  K  M

601 TGAAAAATAGTGGCCGTAGCAACAAGGTTGCACGTACTTCTCCCATCAACCTCGGCTTGA
     K  N  S  G  R  S  N  K  V  A  R  T  S  P  I  N  L  G  L  N

661 ATGTGAATGACCTCTTGAAGCAGAAAGCCATCTCTTCCTCAATGCACTCTCTGTATGGGC
     V  N  D  L  L  K  Q  K  A  I  S  S  S  M  H  S  L  Y  G  L

721 TTGGCTTGGGTAGCCAGCAGCAGCCACAGCAACAGCAGCAGCCAGCCCAGCCGCCACCGC
     G  L  G  S  Q  Q  Q  P  Q  Q  Q  Q  Q  P  A  Q  P  P  P

781 CACCACCACCACCACAGCAGCAACAACAGCAGAAAACCTCTGCTCTTTCTCCTAATGCCA
     P  P  P  P  Q  Q  Q  Q  Q  Q  K  T  S  A  L  S  P  N  A  K
```

FIG.1A

```
841  AGGAATTTATTTTTCCTAATATGCAGGGTCAAGGTAGTAGTACCAATGGAATGTTCCCAG
      E  F  I  F  P  N  M  Q  G  Q  G  S  S  T  N  G  M  F  P  G

901  GTGACAGCCCCCTTAACCTCAGTCCTCTCCAGTACAGTAATGCCTTTGATGTGTTTGCAG
      D  S  P  L  N  L  S  P  L  Q  Y  S  N  A  F  D  V  F  A  A

961  CCTATGGAGGCCTCAATGAGAAGTCTTTTGTAGATGGCTTGAATTTTAGCTTAAATAACA
      Y  G  G  L  N  E  K  S  F  V  D  G  L  N  F  S  L  N  N  M

1021 TGCAGTATTCTAACCAGCAATTCCAGCCTGTTATGGCTAACTAAAAAAAAGAAAATGTAT
      Q  Y  S  N  Q  Q  F  Q  P  V  M  A  N

1081 CGTACAAGTTAAAATGCACGGGCCAAGGGGGGATTTTTTTTTTCACCTCCTTGAGAATTT
1141 TTTTTTTTTAAGCTTATAGTAAGGATACATTCAAGCTTGGTTAAAAAAATAATAATAAAAC
1201 ATGCATCATTTTTCATTTGCCAACCAAGCACAAAGTTATTTTATGCTGCCTGTATATTTT
1261 AAAGTATACTCTCAGATATGCCCTCTTACAGTATTTTAAGATATTAGCAAAGGACATGGC
1321 TTGATTTTTTTTTATAAAAATTGGCACTAATAAGTGGGTTTATTGGTCTTTTCTAATTGT
1381 ATAATTTAATTTAGTACCAAAGTTTGTAAAATATCAGAGGATATATATATATTGTATCCT
1441 ACGACATGGTATTGCATTTATATCTTTTTACTACAGTGATCTGTGACAGCAGCAGCCTCA
1501 TGTTGTATTTTTTTTACTGAAATTGTAAAATATCCATCTTAAAGACATCAACTATTCTAA
1561 AAATTGTGTACAGGATATTCCTTTAGTGGTGGAATTAAAATGTGCGAATACTTGCTTTCT
1621 CCAAAAAAATGTATTTTCTGTTAAAAGTTTAAAGATTTTTGCTATATATTATGGAAGGAA
1681 AATGTAATCGTAAATATTAATTTTGTACCTATATTGTGCAATACTTGAAAAAAACGGTAT
1741 AAAAGTATTTTGAGTCAGTGTCTTACATGTTAAGAGGGACTGAAATAGTTTATATTAAGT
1801 TTGTATTAAAATTCTTTAAAATTAAAAAAAAAAAAAAAAAAA
```

FIG.1B

```
  1 GGAATTCGGCACGAGCAACCCTCAACGACGAAAAGGACTTCGGTCCCCTGGCCCGGCGAC
 61 GCCCGGGAAGGAAAGGAGAGCGACCTCCGCCCCGCGCTCAGGCCACCCTGGAGGGAGAAG
121 CCGCCCCGCGCSSGSGTTAGAGCGCCCCGCCGCCCCGTAGACCCGAAGCCGCCTGGAGCC
181 CAAGGCTGTACACGTGCCCTGTGCTGATTCTCTGCCTAGGAAAGGACCATGCAGCTAGAG
                                                   M  Q  L  E

241 ATCAAAGTGGCCCTGAACTTCATCATCTCCTACTTGTACAACAAGCTGCCCCGGCGCCGG
     I  K  V  A  L  N  F  I  I  S  Y  L  Y  N  K  L  P  R  R  R

301 GCAGACCTGTTTGGGGAGGAGCTAGAGCGGCTTTTGAAAAGGAAATATGAAGGCCACTGG
     A  D  L  F  G  E  E  L  E  R  L  L  K  R  K  Y  E  G  H  W

361 TACCCTGAGAAGCCACTGAAAGGCTCTGGCTTCCGCTGTGTTCACATTGGGGAGATGGTG
     Y  P  E  K  P  L  K  G  S  G  F  R  C  V  H  I  G  E  M  V

421 GACCCCGTGGTGGAGCTGGCCGCCAAGCGGAGTGGCCTGGCGGTGGAAGATGTGCGGGCC
     D  P  V  V  E  L  A  A  K  R  S  G  L  A  V  E  D  V  R  A

481 AATGTGCCTGAGGAGCTGAGTGTCTGGATTGATCCCTTTGAGGTGTCCTACCAGATTGGT
     N  V  P  E  E  L  S  V  W  I  D  P  F  E  V  S  Y  Q  I  G

541 GAGAAGGGAGCTGTGAAAGTGCTGTACCTGGATGACAGTGAGGGTTGCGGTGCCCCAGAG
     E  K  G  A  V  K  V  L  Y  L  D  D  S  E  G  C  G  A  P  E

601 CTGGACAAGGAGATCAAGAGCAGCTTCAACCCTGACGCCCAGGTGTTCGTGCCCATTGGC
     L  D  K  E  I  K  S  S  F  N  P  D  A  Q  V  F  V  P  I  G

661 AGCCAGGACAGCTCCCTGTCCAACTCCCCATCGCCATCCTTTGGCCAGTCACCCAGCCCT
     S  Q  D  S  S  L  S  N  S  P  S  P  S  F  G  Q  S  P  S  P

721 ACCTTCATTCCCCGCTCCGCTCAGCCCATCACCTTCACCACCGCCTCCTTCGCTGCCACC
     T  F  I  P  R  S  A  Q  P  I  T  F  T  T  A  S  F  A  A  T

781 AAATTTGGCTCCACTAAGATGAAGAAGGGGGGCGGGGCAGCAAGTGGTGGGGGTGTAGCC
     K  F  G  S  T  K  M  K  K  G  G  G  A  A  S  G  G  G  V  A

841 AGCAGTGGGGCGGGTGGCCAGCAGCCACCACAGCAGCCTCGCATGGCCCGCTCACCCACC
     S  S  G  A  G  G  Q  Q  P  P  Q  Q  P  R  M  A  R  S  P  T
```

FIG.2A

```
901  AACAGCCTGCTGAAGCACAAGAGCCTCTCTCTGTCTATGCATTCACTGAACTTCATCACG
      N  S  L  L  K  H  K  S  L  S  L  S  M  H  S  L  N  F  I  T

961  GCCAACCCGGCCCCTCAGTCCCAGCTCTCACCCAATGCCAAGGAGTTCGTGTACAACGGT
      A  N  P  A  P  Q  S  Q  L  S  P  N  A  K  E  F  V  Y  N  G

1021 GGTGGCTCACCCAGCCTCTTCTTTGATGCGGCCGATGGCCAGGGCAGCGGCACCCCAGGC
      G  G  S  P  S  L  F  F  D  A  A  D  G  Q  G  S  G  T  P  G

1081 CCGTTTGGAGGCAGTGGGGCTGGCACCTGCAACAGCAGCAGCTTTGACATGGCCCAGGTA
      P  F  G  G  S  G  A  G  T  C  N  S  S  S  F  D  M  A  Q  V

1141 TTTGGAGGTGGTGCCAACAGCCTCTTCCTGGAGAAGACACCCTTTGTGGAAGGCCTCAGC
      F  G  G  G  A  N  S  L  F  L  E  K  T  P  F  V  E  G  L  S

1201 TACAACCTGAACACCATGCAGTATCCCAGCCAGCAGTTCCAGCCCGTGGTGCTGGCCAAC
      Y  N  L  N  T  M  Q  Y  P  S  Q  Q  F  Q  P  V  V  L  A  N

1261 TGACCATCTACCTGGCCCGTGGGGGCAGGAGCACCCAAGACCACAGAAAAGAGAAAGGAA
1321 AGGCCAAAAAAAAAAAAAAAAAAA   1343
```

FIG.2B

```
              1                                                    50
     BTG2  .......... MQLEIQVALN FIISYLYNK. .LPRRRVNIF GEELERLLKK
     BTG3  .......... MQLEIKVALN FIISYLYNK. .LPRRRADLF GEELERLLKR
     BTG1  MHPFYTRAAT MIGEIAAAVS FISKFLRTKG LTSERQLQTF SQSLQELLAE
Consensus  ---------- MQLEI-VALN FIISYLYNK- -LPRRR---F GEELERLLK- 51                                                  100
     BTG2  KYEGHWYPEK PYKGSGFRCI HIGEKVDPVI EQASKESGLD IDDVRGNLPQ
     BTG3  KYEGHWYPEK PLKGSGFRCV HIGEMVDPVV ELAAKRSGLA VEDVRANVPE
     BTG1  HYKHHWFPEK PCKGSGYRCI RINHKMDPLI GQAAQRIGLS SQELFRLLPS
Consensus  KYEGHWYPEK P-KGSGFRCI HIGEKVDPVI EQAAKRSGL- --DVR-NLP- 101                                                 150
     BTG2  DLSVWIDPFE VSYQIGEKGP VKVLYVDDNN ENGC.ELD.. KEIKNSFNPE
     BTG3  ELSVWIDPFE VSYQIGEKGA VKVLYLDDSE GCGAPELD.. KEIKSSFNPD
     BTG1  ELTLWVDPYE VSYRIGEDGS ICVLYEASPA GGSTQNSTNV QMVDSRISCK
Consensus  ELSVWIDPFE VSYQIGEKG- VKVLY-DD-- G-G--ELD-- KEIKSSFNP- 151                                                 200
     BTG2  AQVFMPISDP ASSVSSSPSP PFGHSAAVSP TFMPRSTQPL TFTTATFAAT
     BTG3  AQVFVPIGSQ DSSLSNSPSP SFGQSP..SP TFIPRSAQPI TFTTASFAAT
     BTG1  EELLLG.... ....RTSPSK NYNMMTVSG. .......... ..........
Consensus  AQVF-PI--- -SS-S-SPSP -FG-S---SP TF-PRS-QP- TFTTA-FAAT 201                                                 250
     BTG2  KFGSTKMKNS GRSNKVARTS PINLGLN... .........V NDLLKQKAIS
     BTG3  KFGSTKMKKG GGAASGGGVA SSGAGGQQPP QQPRMARSPT NSLLKHKSLS
     BTG1  .......... .......... .......... .......... ..........
Consensus  KFGSTKMK-- G--------- ----G----- ---------- N-LLK-K--S 251                                                 300
     BTG2  SSMHSLYGLG LGSQQQPQQQ QQPAQPPPPP PPPQQQQQQK TSALSPNAKE
     BTG3  LSMHSLNFIT ANPAPQSQ.. .......... .......... ...LSPNAKE
     BTG1  .......... .......... .......... .......... ..........
Consensus  -SMHSL---- -----Q-Q-- ---------- ---------- ---LSPNAKE
```

FIG. 3A

```
              301                                                           350
BTG2    FI........  ..FPNMQGQG  SSTNGMFPGD  SPL..NLSPL  QYSNAFDVFA
BTG3    FVYNGGGSPS  LFFDAADGQG  SGTPGPFGGS  GAGTCNSSSF  DMAQVFGGGA
BTG1    ..........  ..........  ..........  ..........  ..........
Consensus  F---------  --F----GQG  S-T-G-F-G-  -----N-S--  -----F---A 351                                 385
BTG2    AYGGLNEKSF  VDGLNFSLNN  MQYSNQQFQP  .VMAN
BTG3    NSLFLEKTPF  VEGLSYNLNT  MQYPSQQFQP  VVLAN
BTG1    ..........  ..........  ..........  .....
Consensus  ----L----F  V-GL---LN-  MQY--QQFQP  -V-AN
```

FIG.3B

DIAGNOSTIC METHODS BASED ON HUMAN BTG-2 AND BTG-3 POLYPEPTIDES

The present application is a divisional of U.S. application Ser. No. 09/843,846, filed Apr. 30, 2001 (now U.S. Pat. No. 6,689,360), which is herein incorporated by reference, which is a divisional of U.S. application Ser. No. 09/221,844, filed Dec. 29, 1998 (now U.S. Pat. No. 6,258,777), which is herein incorporated by reference; said U.S. patent application Ser. No. 09/221,844 is a divisional of U.S. application Ser. No. 08/718,738, filed Sep. 18, 1996 (now U.S. Pat. No. 6,013,469), which is herein incorporated by reference; said U.S. patent application Ser. No. 08/718,738 is a continuation-in-part (CIP) of U.S. patent application Ser. No. 08/463,382, filed Jun. 5, 1995, now abandoned, which is herein incorporated by reference; U.S. patent application Ser. No. 08/718,738 is also a CIP of U.S. patent application Ser. No. 08/460,104, filed Jun. 2, 1995, now abandoned, which is herein incorporated by reference; said U.S. patent application Ser. Nos. 08/463,382 and 08/460,104 are CIPs of International Application No. PCT/US95/03323, filed Mar. 17, 1995, which is herein incorporated by reference.

BACKGROUND OF THE INVENTION

1. Field of the Invention

The present invention relates to novel antiproliferative genes. More specifically, isolated nucleic acid molecules are provided encoding the human B-cell translocation genes 2 and 3 (BTG-2 and BTG-3). BTG-2 and BTG-3 polypeptides are also provided, as are vectors, host cells and recombinant methods for producing the same.

2. Related Art

In normal tissues, homeostasis is maintained through negative and positive growth controls which effect the proliferation and differentiation related to cellular genetic programs. An alteration of this subtle balance can result in developmental abnormalities or in neoplasia. Proto-oncogenes, genes that promote cell division, were the first growth-inducing elements to be identified and more than sixty of them have been described so far (Bishop, J. M., Cell 64:235–248 (1991)). The genes that negatively regulate cell proliferation are crucial to counteract the growth-inducing elements and are likely to have the same importance as proto-oncogenes in controlling cell division (Marshall, C. J., Cell 64:313–326 (1991)), especially since the loss of their function has been reported to be associated with irregular cellular differentiation and proliferation or with alteration of embryonic development (Weinberg, R. A., Science 254:1138–1146 (1991)).

The polynucleotides and polypeptides of the present invention are thought to be members of a family of antiproliferative genes. BTG-1 is a member of this group and has been cloned and expressed. (Rovault, J. P. et al., The EMBO Journal 11(4):1663–1670 (1992)). BTG-1 was shown to negatively regulate N1H3T3 cell proliferation when over-or inappropriately expressed. BTG stands for B-cell translocation gene, and the BTG-1 gene has been shown to be involved in a chromosomal translocation [t(8;12)(q24;22)] in B-cell chronic lymphocytic leukemia.

The BTG-1 open reading frame is 60% homologous to PC3, an immediate early gene induced by nerve growth factor in rat PC12 cells. Sequence and Northern blot analyses indicate that BTG-1 and PC3 are not cognate genes but are thought to be members of this new family of anti-proliferation genes. The BTG-1 gene is preferentially expressed in quiescent cells during the early sub-phases of $G_1$ in a serum-dependent manner and it is then down-regulated to reach a minimum level as the cells enter the S phase. This suggests a functional link between BTG-1 and the cell cycle process. BTG-1 is expressed in tissues (lymphoid, liver, placenta) containing non-dividing cells likely to re-enter the cell cycle upon different stimuli, whereas the expression of BTG-1 is barely detectable in fully differentiated tissues such as brain and muscle.

The BTG-1 gene was shown to be highly conserved in evolution and a similar 1.8 Kb transcript can be detected in murine and chicken tissue by using a human BTG-1 DNA probe (Rimokh, R. et al., Genes Chrom. Cancer 3:24–36 (1991)).

The BTG-2 and BTG-3 genes and gene products have been putatively identified as members of this family as a result of amino acid sequence homology to BTG-1.

SUMMARY OF THE INVENTION

The present invention provides isolated nucleic acid molecules comprising a polynucleotide encoding the BTG-2 or BTG-3 polypeptide having the amino acid sequences shown in FIG. 1A–1B (SEQ ID NO:2) and FIG. 2A–2B (SEQ ID NO:4), respectively, or having the amino acid sequences encoded by the cDNA clones deposited in bacterial hosts as ATCC™ Deposit Number 97025 on Jan. 17, 1995 (BTG-2) and ATCC™ Deposit Number 97010 on Jan. 5, 1995 (BTG-3). For BTG-2, the nucleotide sequence determined by sequencing the deposited cDNA clone contains an open reading frame encoding a polypeptide of about 345 amino acid residues, with a predicted leader sequence of about 25 amino acid residues such that the mature protein comprises about 320 amino acids. The amino acid sequence of the predicted mature BTG-2 protein is shown in FIG. 1A–1B, amino acid residues from about 26 to about 345 (SEQ ID NO:2).

For BTG-3, the nucleotide sequence determined by sequencing the deposited cDNA clone contains an open reading frame encoding a polypeptide of about 344 amino acid residues, with a predicted leader sequence of about 18 amino acid residues such that the mature protein comprises about 326 amino acids. The amino acid sequence of the predicted mature BTG-3 protein is shown in FIG. 2A–2B, amino acid residues from about 19 to about 344 (SEQ ID NO:4).

Thus, one aspect of the invention provides an isolated nucleic acid molecule comprising a polynucleotide having a nucleotide sequence selected from the group consisting of: (a) a nucleotide sequence encoding the BTG-2 or BTG-3 polypeptide having the complete amino acid sequence in FIG. 1A–1B (SEQ ID NO:2) and FIG. 2A–2B (SEQ ID NO:4), respectively; (b) a nucleotide sequence encoding the mature BTG-2 or mature BTG-3 polypeptide having the amino acid sequence at positions from about 26 to about 345 in FIG. 1A–1B (SEQ ID NO:2) and from about 19 to about 344 in FIG. 2A–2B (SEQ ID NO:4), respectively; (c) a nucleotide sequence encoding the BTG-2 or BTG-3 polypeptide having the complete amino acid sequence encoded by the cDNA clone contained in ATCC™ Deposit No. 97025 and 97010, respectively; (d) a nucleotide sequence encoding the mature BTG-2 or mature BTG-3 polypeptide having the amino acid sequence encoded by the cDNA clone contained in ATCC™ Deposit No. 97025 and 97010, respectively; and (e) a nucleotide sequence complementary to any of the nucleotide sequences in (a), (b), (c) or (d) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d) or (e), above, or a polynucleotide which hybridizes under stringent hybridization conditions to a polynucleotide in (a), (b), (c), (d) or (e), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a BTG-2 or BTG-3 polypeptide having an amino acid sequence in (a), (b), (c) or (d), above.

The present invention also relates to recombinant vectors, which include the isolated nucleic acid molecules of the present invention, and to host cells containing the recombinant vectors, as well as to methods of making such vectors and host cells and for using them for production of BTG-2 or BTG-3 polypeptides or peptides by recombinant techniques.

The invention further provides an isolated BTG-2 or BTG-3 polypeptide having an amino acid sequence selected from the group consisting of: (a) the amino acid sequence of the BTG-2 or BTG-3 polypeptide having the complete 345 and 344 amino acid sequences shown in FIG. 1A–1B (SEQ ID NO:2) and FIG. 2A–2B (SEQ ID NO:4), respectively; (b) the amino acid sequence of the predicted mature BTG-2 or BTG-3 polypeptide (without the leader) having the amino acid sequence at positions from about 26 to about 345 in FIG. 1A–1B (SEQ ID NO:2) and from about 19 to about 344 in FIG. 2A–2B (SEQ ID NO:4), respectively; (c) the amino acid sequence of the BTG-2 or BTG-3 polypeptide having the complete amino acid sequence, including the leader, encoded by the cDNA clone contained in ATCC™ Deposit No. 97025 and 97010, respectively; and (d) the amino acid sequence of the mature BTG-2 or BTG-3 polypeptide having the amino acid sequence encoded by the cDNA clone contained in ATCC™ Deposit No. 97025 and 97010, respectively. The polypeptides of the present invention also include polypeptides having an amino acid sequence with at least 90% similarity, and more preferably at least 95% similarity to those described in (a), (b), (c) or (d) above, as well as polypeptides having an amino acid sequence at least 80% identical, more preferably at least 90% identical, and still more preferably 95%, 96%, 97%, 98% or 99% identical to those above.

An additional embodiment of this aspect of the invention relates to a peptide or polypeptide which has the amino acid sequence of an epitope-bearing portion of a BTG-2 or BTG-3 polypeptide having an amino acid sequence described in (a), (b), (c) or (d), above. Peptides or polypeptides having the amino acid sequence of an epitope-bearing portion of a BTG-2 or BTG-3 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a BTG-2 or BTG-3 polypeptide having an amino acid sequence described in (a), (b), (c) or (d) above. Such antibodies are useful diagnostically or therapeutically as describe below.

In accordance with yet a further aspect of the present invention, there is provided a process for utilizing such polypeptides, or polynucleotides encoding such polypeptides for therapeutic purposes, for example, to treat disease states characterized by aberrant cellular proliferation, and to modulate cellular growth.

In accordance with yet another aspect of the present invention, there are provided antagonists to such polypeptides, which may be used to inhibit the action of such polypeptides, for example, in the treatment of diseases related to chromosomal translocation, for example, lymphocytic leukemia.

In accordance with still another aspect of the present invention, there are provided diagnostic assays for detecting diseases related to the under-expression of the polypeptides of the present invention and mutations in the nucleic acid sequences encoding such polypeptides.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

BRIEF DESCRIPTION OF THE FIGURES

FIG. 1A–1B is an illustration of the cDNA and corresponding deduced amino acid sequence of BTG-2. One-letter abbreviations for amino acids are used. Sequencing was performed, for both BTG-2 and BTG-3, using a 373 Automated DNA sequencer (Applied Biosystems, Inc.). Sequencing accuracy is predicted to be greater than 97% accurate.

FIG. 2A–2B shows the cDNA and corresponding deduced amino acid sequence of the putative BTG-3.

FIG. 3A–3B is an amino acid sequence alignment between BTG-1, BTG-2 and BTG-3 proteins.

DETAILED DESCRIPTION OF THE INVENTION

The present invention provides isolated nucleic acid molecules comprising a polynucleotide encoding a BTG-2 or BTG-3 polypeptide having the amino acid sequence shown in FIG. 1A–1B (SEQ ID NO:2) and FIG. 2A–2B (SEQ ID NO:4), respectively, which were determined by sequencing cloned cDNAs. The BTG-2 and BTG-3 proteins of the present invention share sequence homology with each other and with BTG-1 (FIG. 3A–3B) (SEQ ID NO:17 (BTG-I sequence) and SEQ ID NO:18 (consensus sequence). The nucleotide sequences shown in FIG. 1A–1B (SEQ ID NO:1) and FIG. 2A–2B (SEQ ID NO:3) were obtained by sequencing the above described cDNA clones, which were deposited at the American Type Culture Collection, 10801 University Blvd., Manassas, Va. 20110-2209, USA, and given the accession numbers indicated above. The deposited clones are contained in the PBLUESCRIPT™ SK(−) plasmid (STRATAGENE™, LaJolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 or SEQ ID NO:3 set forth using deoxyribonucleotide abbreviations is intended to indicate an RNA molecule having a sequence in which each deoxyribonucleotide A, G or C of SEQ ID NO:1 or SEQ ID NO:3 has been replaced by the corresponding ribonucleotide A, G or C, and each deoxyribonucleotide T has been replaced by a ribonucleotide U.

Using the information provided herein, such as the nucleotide sequence in FIG. 1A–1B or FIG. 2A–2B, a nucleic acid molecule of the present invention encoding a BTG-2 or BTG-3 polypeptide may be obtained using standard cloning and screening procedures, such as those for cloning cDNAs using mRNA as starting material. Illustrative of the invention, the nucleic acid molecules described in FIG. 1A–1B (SEQ ID NO:1) and FIG. 2A–2B (SEQ ID NO:3) were discovered in cDNA libraries derived from a human endometrial tumor and a human synovial carcinoma, respectively. For BTG-2, the gene can also be identified in cDNA libraries from the following tissues: liver, lymphoid and placenta. For BTG-3, the gene can also be identified in cDNA libraries from the following tissues: synovial sarcoma, cerebellum, embryonic, and placenta.

The determined nucleotide sequence of the BTG-2 cDNA of FIG. 1A–1B (SEQ ID NO:1) contains an open reading frame encoding a protein of about 345 amino acid residues and a predicted leader sequence of about 25 amino acid residues. The amino acid sequence of the predicted mature BTG-2 protein is shown in FIG. 1A–1B (SEQ ID NO:2), amino acid residue from about 26 to about 345. The BTG-2 protein shown in FIG. 1A–1B (SEQ ID NO:2) is about 49% identical and about 72% similar to BTG-1 over a 91 amino acid stretch (FIG. 3A–3B).

The determined nucleotide sequence of the BTG-3 cDNA of FIG. 2A–2B (SEQ ID NO:3) contains an open reading frame encoding a protein of about 344 amino acid residues and a predicted leader sequence of about 18 amino acid residues. The amino acid sequence of the predicted mature BTG-3 protein is shown in FIG. 2A–2B (SEQ ID NO:4), amino acid residue from about 19 to about 344. The BTG-3 protein shown in FIG. 2A–2B (SEQ ID NO:4) is about 41% identical and about 74% similar to BTG-1 over an 85 amino acid stretch (FIG. 3A–3B). Over the same stretch of 85 amino acids, BTG-2 and BTG-3 are 83% identical and 87% similar to each other. In addition, BTG-2 is approximately 143 amino acids longer at the carboxy terminus as compared to BTG-1, while BTG-3 is approximately 162 amino acids longer at the carboxy terminus. Both BTG-2 and BTG-3 contain unique regions rich in the amino acids proline and glutamine.

As indicated, the present invention also provides mature forms of the BTG-2 and BTG-3 proteins. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides nucleotide sequences encoding the mature BTG-2 and BTG-3 polypeptides having the amino acid sequences encoded by the cDNA clones contained in the hosts identified as ATCC™ Deposit No. 97025 and 97010, respectively.

By the mature BTG-2 and BTG-3 polypeptides having the amino acid sequences encoded by the deposited cDNA clones is meant the mature forms of these proteins produced by expression in a mammalian cell (e.g., COS cells, as described below) of the complete open reading frame encoded by the human DNA, sequence of the clones contained in the vectors in the deposited hosts. As indicated below, the mature BTG-2 and BTG-3 polypeptides having the amino acid sequences encoded by the deposited cDNA clones may or may not differ from the predicted "mature" BTG-2 and BTG-3 polypeptides shown in FIG. 1A–1B and FIG. 2A–2B, respectively. This depends on the accuracy of the predicted cleavage site based on computer analysis.

Methods for predicting whether a protein has a secretory leader as well as the cleavage point for that leader sequence are available because it is known that much of the cleavage specificity for a secretory protein resides in certain amino acid residues within the signal sequence and the N-terminus of the mature protein, particularly residues immediately surrounding the cleavage site. For instance, the method of McGeoch (Virus Res. 3:271–286 (1985)) uses the information from a short N-terminal charged region and a subsequent uncharged region of the complete (uncleaved) protein. The method of von Heinje (Nucleic Acids Res. 14:46834690 (1986)) uses the information from the residues surrounding the cleavage site, typically residues −13 to +2 where +1 indicates the amino acid terminus of the mature protein. The accuracy of predicting the cleavage points of known mammalian secretory proteins for each of these methods is in the range of 75–80%. von Heinje, supra. However, the two methods do not always produce the same predicted cleavage point(s) for a given protein.

Thus, in view of above, as one of ordinary skill would appreciate, the actual leader sequence of the BTG-2 protein of the present invention is predicted to be about 25 amino acids in length, but may be anywhere in the range of about 15 to about 35 amino acids. Similarly, the actual leader sequence of the BTG-3 protein of the present invention is predicted to be about 18 amino acids in length, but may be anywhere in the range of about 8 to about 28 amino acids. Further, due to possible sequencing errors as discussed above, the full-length BTG-2 protein is predicted to be about 345 amino acids in length, but may be in the range of about 335 to about 355 amino acids. Similarly, the full-length BTG-3 protein is predicted to be about 344 amino acids in length, but may be in the range of about 335 to about 355 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules shown in FIG. 1A–1B (SEQ ID NO:1) and FIG. 2A–2B (SEQ ID NO:3); DNA molecules comprising the coding sequence for the mature BTG-2 and BTG-3 proteins shown in FIG. 1A–1B (SEQ ID NO:2) and FIG. 2A–2B (SEQ ID NO:3), respectively; and DNA molecules which comprise a sequence substantially different from those described above but which, due to the degeneracy of the genetic code, still encode the BTG-2 or BTG-3 protein. Of course, the genetic code is well known in the art. Thus, it would be routine for one skilled in the art to generate such degenerate variants.

In another aspect, the invention provides isolated nucleic acid molecules encoding the BTG-2 or BTG-3 polypeptide having an amino acid sequence encoded by the above-described deposited cDNA clones. Preferably, these nucleic acid molecules will encode the mature polypeptides encoded by the deposited cDNA clones. The invention further provides isolated nucleic acid molecules having a sequence complementary to one of the above sequences. Such isolated molecules, particularly DNA molecules, are useful as probes for gene mapping, by in situ hybridization with chromosomes, and for detecting expression of the BTG-2 or BTG-3 gene in human tissue, for instance, by Northern blot analysis.

The present invention is further directed to fragments of the isolated nucleic acid molecules described herein. By a fragment of an isolated nucleic acid molecule having the nucleotide sequence of one of the deposited cDNAs or the nucleotide sequence shown in FIG. 1A–1B (SEQ ID NO:1) or FIG. 2A–2B (SEQ ID NO:2) is intended fragments at least about 15 nt, and more preferably at least about 20 nt, still more preferably at least about 30 nt, and even more preferably, at least about 40 nucleotides in length which are useful as diagnostic probes and primers as discussed herein. Of course, larger fragments 50–1500 nucleotides in length are also useful according to the present invention as are fragments corresponding to most, if not all, of the nucleotide sequences of the deposited cDNAs or as shown in FIG. 1A–1B (SEQ ID NO:1) or FIG. 2A–2B (SEQ ID NO:2). By a fragment at least 20 nucleotides in length, for example, is intended fragments which include 20 or more contiguous bases from the nucleotide sequences of the deposited cDNA or the nucleotide sequence as shown in FIG. 1A–1B (SEQ ID NO:1) or FIG. 2A–2B (SEQ ID NO:2). Since the BTG-2 and BTG-3 genes have been deposited and the nucleotide sequences shown in FIG. 1A–2B (SEQ ID NO:1) and FIG. 2A–2B (SEQ ID NO:3) are provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding epitope-bearing portions of the BTG-2 or BTG-3 protein. Methods for generating such epitope-bearing portions of the BTG-2 or BTG-3 protein are described in detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC™ Deposit No. 97025 or 97010. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 50–750 nt in length, or even to the entire length of the reference polynucleotide, are also useful as probes according to the present invention, as are polynucleotides corresponding to most, if not all, of the nucleotide sequence of the deposited cDNAs or the nucleotide sequence as shown in FIG. 1A–1B (SEQ ID NO:1) or FIG. 2A–2B (SEQ ID NO:3). By a portion of a polynucleotide of "at least 20 nucleotides in length," for example, is intended 20 or more contiguous nucleotides from the nucleotide sequence of the reference polynucleotide. As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual*, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference. Of course, a polynucleotide which hybridizes only to a poly A sequence (such as the 3' terminal poly(A) tract of the BTG-2 or BTG-3 cDNA shown in FIG. 1A–1B (SEQ ID NO:1)) and FIG. 2A–2B (SEQ ID NO:2), respectively, or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a BTG-2 or BTG-3 polypeptide may include, but are not limited to those encoding the amino acid sequence of the mature polypeptide, by itself; the coding sequence for the mature polypeptide and additional sequences, such as those encoding the leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the BTG-2 or BTG-2 protein fused to Fc at the N- or C-terminus.

The present invention further relates to variants of the nucleic acid molecules of the present invention, which encode portions, analogs or derivatives of the BTG-2 or BTG-3 protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the BTG-2 or BTG-3 protein or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to: (a) a nucleotide sequence encoding the BTG-2 or BTG-3 polypeptide having the complete amino acid sequence in FIG. 1A–1B (SEQ ID NO:2) and FIG. 2A–2B (SEQ ID NO:4), respectively; (b) a nucleotide sequence encoding the mature BTG-2 or mature BTG-3 polypeptide having the amino acid sequence at positions from about 26 to about 345 in FIG. 1A–1B (SEQ ID NO:2) and from about 19 to about 344 in FIG. 2A–2B (SEQ ID NO:4), respectively; (c) a nucleotide sequence encoding the BTG-2 or BTG-3 polypeptide having the complete amino acid sequence encoded by the cDNA clone contained in ATCC™ Deposit No. 97025 and 97010, respectively; (d) a nucleotide sequence encoding the mature BTG-2 or mature BTG-3 polypeptide having the amino acid sequence encoded by the cDNA clone contained in ATCC™ Deposit No. 97025 and 97010, respectively; and (e) a nucleotide sequence complementary to any of the nucleotide sequences in (a), (b), (c) or (d) above.

By a polynucleotide having a nucleotide sequence at least, for example, 95% "identical" to a reference nucleotide sequence encoding a BTG-2 or BTG-3 polypeptide is intended that the nucleotide sequence of the polynucleotide is identical to the reference sequence except that the polynucleotide sequence may include up to five point mutations per each 100 nucleotides of the reference nucleotide sequence encoding the BTG-2 or BTG-3 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1A–1B or FIG. 3A–3B or to the nucleotide sequence of one of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1A–1B (SEQ ID NO:1) or FIG. 3A–3B (SEQ ID NO:3) or to the nucleic acid sequence of one of the deposited cDNAs, irrespective of whether they encode a polypeptide having BTG-2 or BTG-3 activity. This is because even where a particular nucleic acid molecule does not encode a polypeptide having BTG-2 or BTG-3 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having BTG-2 or BTG-3 activity include, inter alia, (1) isolating the BTG-2 or BTG-3 gene or allelic variants thereof in a cDNA library; (2) in situ hybridization (e.g., "FISH") to metaphase chromosomal spreads to provide precise chromosomal location of the BTG-2 or BTG-3 gene, as described in Verma et al., *Human Chromosomes: A Manual of Basic Techniques,* Pergamon Press, New York (1988); and Northern Blot analysis for detecting BTG-2 or BTG-3 mRNA expression in specific tissues.

Preferred, however, are nucleic acid molecules having sequences at least 90%, 95%, 96%, 97%, 98% or 99% identical to the nucleic acid sequence shown in FIG. 1A–1B (SEQ ID NO:1) or FIG. 2A–2B (SEQ ID NO:3) or to the nucleic acid sequence of one of the deposited cDNAs which do, in fact, encode a polypeptide having BTG-2 or BTG-3 protein activity. By "a polypeptide having BTG-2 or BTG-3 activity" is intended polypeptides exhibiting activity similar, but not necessarily identical, to an activity of the BTG-2 or BTG-3 protein of the invention (either the full-length protein or, preferably, the mature protein), as measured in a particular biological assay. For example, the BTG-2 and BTG-3 proteins are antiproliferative agents. In fact, exogenously expressed BTG-2 protein has been shown to suppress growth of NIH3T3 cells (Matsuda et al., *Oncogene* 12:705–713 (1996)). Thus, BTG-2 or BTG-3 protein activity can be assayed by measuring the ability of a candidate polypeptide to suppress growth of certain cell types in vitro, such as NIH3T3 cells.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1A–1B (SEQ ID NO:1) will encode a polypeptide "having BTG-2 or BTG-3 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having BTG-2 or BTG-3 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

Vectors and Host Cells

The present invention also relates to vectors which include the isolated DNA molecules of the present invention, host cells which are genetically engineered with the recombinant vectors, and the production of BTG-2 and BTG-3 polypeptides or fragments thereof by recombinant techniques.

Recombinant constructs may be introduced into host cells using well known techniques such infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate transacting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from STRATAGENE™; and ptrc99a, pKK223-3, pKK233-3, pDR540, pRIT5 available from PHARMACIA™. Among preferred eukaryotic vectors are pWLNEO, pSV2CAT, pOG44, pXT1 and pSG available from STRATAGENE™; and pSVK3, pBPV, pMSG and pSVL available from PHARMACIA™. Other suitable vectors will be readily apparent to the skilled artisan.

Among known bacterial promoters suitable for use in the present invention include the E. coli lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5- has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The BTG-2 and BTG-3 proteins can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

BTG-2 and BTG-3 Polypeptides and Fragments

The invention further provides an isolated BTG-2 or BTG-3 polypeptide having the amino acid sequence encoded by the deposited cDNAs, or the amino acid sequence in FIG. 1A–1B (SEQ ID NO:2) or FIG. 2A–2B (SEQ ID NO:4), or a peptide or polypeptide comprising a portion of the above polypeptides. The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the BTG-2 or BTG-3 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the BTG-2 or BTG-3 polypeptide which show substantial BTG-2 or BTG-3 polypeptide activity or which include regions of BTG-2 or BTG-3 protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Examples of conservative amino acid substitutions known to those skilled in the art are set forth below:

| Aromatic: | phenylalanine |
| | tryptophan |
| | tyrosine |
| Hydrophobic: | leucine |
| | isoleucine |
| | valine |
| Polar: | glutamine |
| | asparagine |
| Basic: | arginine |
| | lysine |
| | histidine |
| Acidic: | aspartic acid |
| | glutamic acid |
| Small: | alanine |
| | serine |
| | threonine |
| | methionine |
| | glycine |

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990).

The polypeptides of the present invention are preferably provided in an isolated form, and preferably are substantially purified. A recombinantly produced version of the BTG-2 or BTG-3 polypeptide can be substantially purified by the one-step method described in Smith and Johnson, Gene 67:31–40 (1988).

The polypeptides of the present invention include the BTG-2 or BTG-3 polypeptide encoded by the deposited cDNA clones (ATCC™ Nos. 97025 and 97010, respectively) including the leader, the mature polypeptide encoded by the deposited the cDNA clones minus the leader (i.e., the mature protein), the BTG-2 polypeptide of FIG. 1A–1B (SEQ ID NO:2) including the leader, the BTG-3 polypeptide of FIG. 2A–2B (SEQ ID NO:4) including the leader, the BTG-2 polypeptide of FIG. 1A–1B (SEQ ID NO:2) minus the leader, the BTG-3 polypeptide of FIG. 2A–2B (SEQ ID NO:4) minus the leader, as well as polypeptides which have at least 90% similarity, more preferably at least 95% similarity, and still more preferably at least 96%, 97%, 98% or 99% similarity to those described above. Further polypeptides of the present invention include polypeptides at least 80% identical, more preferably at least 90% or 95% identical, still more preferably at least 96%, 97%, 98% or 99% identical to the BTG-2 or BTG-3 polypeptide encoded by the deposited cDNA clones (ATCC™ Nos. 97025 and 97010, respectively), to the BTG-2 polypeptide of FIG. 1A–1B (SEQ ID NO:2), to the BTG-3 polypeptide of FIG. 2A–2B (SEQ ID NO:4) and also include portions of such BTG-2 or BTG-3 polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482489, 1981) to find the best segment of similarity between two sequences.

By a polypeptide having an amino acid sequence at least, for example, 95% "identical" to a reference amino acid sequence of a BTG-2 or BTG-3 polypeptide is intended that the amino acid sequence of the polypeptide is identical to the reference sequence except that the polypeptide sequence may include up to five amino acid alterations per each 100 amino acids of the reference amino acid of the BTG-2 or BTG-3 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1A–1B (SEQ ID NO:2), FIG. 2A–2B (SEQ ID NO:4) or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The BTG-2 or BTG-3 polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting BTG-2 or BTG-3 protein expression as described below or as agonists and antagonists capable of enhancing or inhibiting BTG-2 or BTG-3 protein function. Further, such polypeptides can be used in the yeast two-hybrid system to "capture" BTG-2 or BTG-3 protein binding proteins which are also candidate agonist and antagonist according to the present invention. The yeast two hybrid system is described in Fields and Song, Nature 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol.* 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–C-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, BTG-2 or BTG-3 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84–86 (1988)). Fusion proteins that have a disulfide-linked dimeric structure due to the IgG part can also be more efficient in binding and neutralizing other molecules than the monomeric BTG-2 or BTG-3 protein or protein fragment alone (Fountoulakis et al., J Biochem 270:3958–3964 (1995)).

Diagnostic and Therapeutic Uses

The BTG-2 and BTG-3 polypeptides have an anti-proliferative ability and may be employed to treat diseases or pathological conditions associated with aberrant cellular proliferation. The polypeptides may be employed as a tumor/growth suppression regulator. They may also be employed to inhibit cancer cell proliferation.

BTG-2 and BTG-3 may also be employed to prevent uncontrolled wound healing which would otherwise cause scarring. Restenosis, which is re-occlusion of arterial walls after balloon angioplasty, may also be treated with BTG-2 and BTG-3 since arteries re-occlude through cell proliferation. Similarly angiogenesis of tumors may be inhibited.

The BTG-2 and BTG-3 genes and gene products may also be employed for modulation of cellular growth. Due to their anti-proliferative effect they could be selectively administered or possibly inhibited when it is desirable to have certain cells proliferate. An example would be a disorder related to the underproduction of certain cells, where proliferation and differentiation of these cells would help to treat the disorder.

The polynucleotides and polypeptides encoded by such polynucleotides may also be utilized for in vitro purposes related to scientific research, synthesis of DNA and manufacture of DNA vectors and for designing therapeutics and diagnostics for the treatment of human disease.

The nucleic acid sequences of the present invention may be employed as part of a diagnostic assay for detecting susceptibility to diseases associated with aberrant cellular proliferation. Since, the polypeptides of the present invention are encoded by anti-proliferative genes, a disruption in the transcription of the genes and corresponding lack of production of the gene product will likely be involved in aberrant cellular proliferation associated with a malignant phenotype.

Individuals carrying mutations in the genes may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature 324:163–166 (1986)) prior to analysis. RNA or cDNA may also be used for the same purpose. As an example, PCR primers complementary to the nucleic acid encoding the polypeptides of the present invention can be used to identify and analyze mutations. For example, deletions and insertions can be detected by a change in size of the amplified product in comparison to the normal genotype. Point mutations can be identified by hybridizing amplified DNA to radiolabeled RNA of the present invention or alternatively, radiolabeled antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science 230:1242 (1985)).

Sequence changes at specific locations may also be revealed by nuclease protection assays, such as RNase and SI protection or the chemical cleavage method (e.g., Cotton et al., *Proc. Natl. Acad. Sci.* (*USA*) 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the proteins of the present invention in various tissues since an over-expression of the proteins compared to normal control tissue samples may detect the presence of a disease or susceptibility to a disease, for example, abnormal cellular proliferation and differentiation. Assays used to detect levels of these proteins in a sample derived from a host are well-known to those of skill in the art and include radioimmunoassays, competitive-binding assays, Western Blot analysis, ELISA assays and "sandwich" assay. An ELISA assay (Coligan et al., *Current Protocols in Immunology* 1(2), Chapter 6, (1991)) initially comprises preparing an antibody specific to the antigens to the polypeptides of the present invention, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein, for example, bovine serum albumen. Next, the monoclonal antibody specific to the polypeptides of the present invention is incubated in the dish during which time the monoclonal antibodies attach to any proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to the proteins of the present invention. Unattached reporter antibody is then washed out. Peroxidase substrates are then added to the dish and the amount of color developed in a given time period is a measurement of the amount of protein present in a given volume of patient sample when compared against a standard curve.

A competition assay may be employed wherein antibodies specific to the polypeptides of the present invention are attached to a solid support. Labeled polypeptides and a sample derived from the host are then passed over the solid support and the amount of label detected, for example by liquid scintillation chromatography, can be correlated to a quantity of the polypeptides of the present invention in the sample.

A "sandwich" assay is similar to an ELISA assay. In a "sandwich" assay the polypeptides of the present invention are passed over a solid support and bind to antibodies attached to a solid support. A second antibody is then bound to the polypeptides. A third antibody which is labeled and specific to the second antibody is then passed over the solid support and binds to the second antibody and an amount can then be quantified.

This invention provides a method for identification of the receptors for the polypeptides of the present invention. The gene encoding the receptor can be identified by numerous methods known to those of skill in the art, for example, ligand panning and FACS sorting (Coligan, et al., *Current Protocols in Immun.* 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photo-affinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein micro-sequencing. The amino acid sequence obtained from micro-sequencing would be used to design a set of degenerate oligonucleotide probes to screen a cDNA library to identify the genes encoding the putative receptors.

Agonists and Antagonists

The present invention further provides a method of identifying agonist and antagonist compounds to the genes and gene products of the present invention. An example of such an assay comprises contacting a mammalian cell or membrane preparation expressing the receptors of the polypeptides with labeled polypeptides, eg. by radioactivity, in the presence of a compound to be screened. The ability of the compound to block and enhance the interaction of the polypeptides of the present invention with its receptor is then measured, for example, by liquid scintillation chromatography.

This invention provides a method of screening drugs to identify those which enhance or inhibit interaction of the polypeptides with their receptors. As an example, a mammalian cell or membrane preparation expressing the receptor would be incubated with labeled polypeptides in the presence of the drug. The ability of the drug to enhance or block this interaction could then be measured.

Alternatively, the response of a known second messenger system following interaction of the polypeptides and their receptors would be measured and compared in the presence or absence of the drug. Such second messenger systems include but are not limited to, cAMP guanylate cyclase, ion channels or phosphoinositide hydrolysis.

Potential antagonists to BTG-2 or BTG-3 polypeptides include an antibody, or in some cases, an oligopeptide, which binds to the polypeptide. Alternatively, a potential antagonist may be a closely related protein which binds to the receptor sites, however, they are inactive forms of the polypeptide and thereby prevent their action since receptor sites are occupied.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., *Nucl. Acids Res.* 6:3073 (1979); Cooney et al, *Science* 241:456 (1988); and Dervan et al., *Science* 251: 1360 (1991)), thereby preventing transcription and the production of BTG-2 and/or BTG-3. The antisense RNA oligonucleotide hybridizes to the mRNA in vivo and blocks translation of the mRNA molecule into the polypeptides (Antisense—Okano, *J. Neurochem.* 56:560 (1991); *Oligodeoxynucleotides as Antisense Inhibitors of Gene Expression*, CRC Press, Boca Raton, Fla. (1988)). The oligonucleotides described above can also be delivered to cells such that the antisense RNA or DNA may be expressed in vivo to inhibit production of the polypeptides of the present invention.

Potential antagonists also include a small molecule which binds to and occupies the active site of the polypeptides thereby making them inaccessible to substrate such that normal biological activity is prevented. Examples of small molecules include but are not limited to small peptides or peptide-like molecules.

The antagonists may be employed to treat leukemia, which results from oncogene activation in hemopoietic cells due to a chromosomal translocation. The polypeptides of the present invention may have a direct or indirect function in the activation of a cellular oncogene resulting in leukemia.

The antagonists may be employed in a composition with a pharmaceutically acceptable carrier, e.g., as hereinafter described.

Modes of Administration

The polypeptides and agonists or antagonists of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides and agonists or antagonists of the present invention may be employed in conjunction with other therapeutic compounds.

The pharmaceutical compositions may be administered in a convenient manner such as by the topical, intravenous, intramuscular or subcutaneous routes. The pharmaceutical compositions are administered in an amount which is effective for treating and/or prophylaxis of the specific indication. In general, they are administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

Gene Therapy

The polypeptides of the present invention, and agonists and antagonists which are polypeptides, may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller et al., *Biotechniques* 7(9):980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human*

Gene Therapy, Vol. 1 (1990), pp. 5–14, which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Chromosome Assay

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases. For a review of this technique, see Verma et al., *Human Chromosomes: A Manual of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man* (available on-line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Antibodies

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, *Nature* 256:495–497 (1975)), the trioma technique, the human B-cell hybridoma technique (Kozbor et al., *Immunology Today* 4:72 (1983)), and the EBV-hybridoma technique to produce human monoclonal antibodies (Cole et al., in *Monoclonal Antibodies and Cancer Therapy,* Alan R. Liss, Inc. (1985), pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., *Nucleic Acids Res.* 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Sambrook, J. et al., *Molecular Cloning: A Laboratory Manual*, Cold Spring Laboratory Press, Cold Spring Harbor, N.Y. (1989), p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

Having generally described the invention, the same will be more readily understood by reference to the following examples, which are provided by way of illustration and are not intended as limiting.

EXAMPLE 1

Cloning and Expression of BTG-2 Using the Baculovirus Expression System

The DNA sequence encoding the full length BTG-2 protein, ATCC™ #97025, is amplified using PCR oligonucleotide primers corresponding to the 5' and 3' end sequences of the gene:

The 5' primer has the sequence 5' CAGTGGATCCGC-CACCATGCAGCTTGAAATCCAAGTAGCAC 3' (SEQ ID No. 5) and contains a Bam HI restriction enzyme site (in bold) followed by 6 nucleotides resembling an efficient signal for the initiation of translation in eukaryotic cells (Kozak, M., J. Mol. Biol., 196:947–950 (1987) and just behind the first 26 nucleotides of the BTG-2 gene (the initiation codon for translation "ATG" is underlined).

The 3' primer has the sequence 5' CAGTGGTACCATA-CATTTTCTTTTTTTTAGTTAGCCAT 3' (SEQ ID No. 6) and contains the cleavage site for the restriction endonuclease Asp718 and 25 nucleotides complementary to the 3' non-translated sequence of the BTG-2 gene. The amplified sequences are isolated from a 1% agarose gel using a commercially available kit ("GENECLEAN™," BIO 101 Inc., La Jolla, Calif.). The fragment is then digested with the endonucleases Bam HI and Asp718 and purified again on a 1% agarose gel. This fragment is designated F2.

The vector pRG1 (modification of pVL941 vector, discussed below) is used for the expression of the BTG-2 protein using the baculovirus expression system (for review see: Summers, M. D. and Smith, G. E., *A manual of methods for baculovirus vectors and insect cell culture procedures*, Texas Agricultural Experimental Station Bulletin No. 1555 (1987)). This expression vector contains the strong polyhedrin promoter of the Autographa californica nuclear polyhidrosis virus (AcMNPV) followed by the recognition sites for the restriction endonucleases. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., *Virology* 170:31–39).

The plasmid is digested with the restriction enzymes Bam HI and Asp718 and dephosphorylated using calf intestinal phosphatase by procedures known in the art. The DNA is then isolated from a 1% agarose gel using the commercially available kit ("GENECLEAN™" BIO 101 Inc., La Jolla, Calif.). This vector DNA is designated V2.

Fragment F2 and the dephosphorylated plasmid V2 are ligated with T4 DNA ligase. *E. coli* HB101 cells are then transformed and bacteria identified that contained the plasmid (pBac BTG-2) with the BTG-2 gene using the respective restriction enzymes. The sequence of the cloned fragment is confirmed by DNA sequencing.

5 μg of the plasmid pBac BTG-2 is co-transfected with 1.0 μg of a commercially available linearized baculovirus ("BACULOGOLD™ baculovirus DNA", Pharmingen, San Diego, Calif.) using the lipofection method (Felgner et al., Proc. Natl. Acad. Sci. (USA) 84:7413–7417 (1987)).

1 μg of BACULOGOLD™ virus DNA and 5 μg of the plasmid pBac BTG-2 are mixed in a sterile well of a microtiter plate containing 50 μl of serum free Grace's medium (Life Technologies Inc., Gaithersburg, Md.). Afterwards 10 μl LIPOFECTIN™ plus 90 μl Grace's medium are added, mixed and incubated for 15 minutes at room temperature. Then the transfection mixture is added drop-wise to the Sf9 insect cells (ATCC™ CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution the viruses are added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-BTG-2 at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labeled proteins visualized by SDS-PAGE and autoradiography.

EXAMPLE 2

Cloning and Expression of BTG-3 Using the Baculovirus Expression System

The DNA sequence encoding the full length BTG-3 protein, ATCC™ #97010, is amplified using PCR oligonucleotide primers corresponding to the 5' and 3' end sequences of the gene:

The 5' primer has the sequence 5' CAGTGGATCCGCACCATGCAGCTAGAGATCAAAGTGGCCC 3' (SEQ ID No:7) and contains a Bam HI restriction enzyme site (in bold) followed by 6 nucleotides resembling an efficient signal for the initiation of translation in eukaryotic cells (Kozak, M., *J. Mol. Biol.* 196:947–950 (1987)) and just behind the first 228 nucleotides of the BTG-3 gene (the initiation codon for translation "ATG" is underlined).

The 3' primer has the sequence 5' CAGTGGTACCACGGGCCAGGTAGATGGTCAGTTGGCCAGCAC 3' (SEQ ID No:8) and contains the cleavage site for the restriction endonuclease Asp718 and 25 nucleotides complementary to the 3' non-translated sequence of the BTG-3 gene. The amplified sequences are isolated from a 1% agarose gel using a commercially available kit ("GENECLEAN™," BIO 101 Inc., La Jolla, Calif.). The fragment is then digested with the endonucleases Barm HI and Asp718 and purified again on a 1% agarose gel. This fragment is designated F2.

The vector pRG1 (modification of pVL941 vector, discussed below) is used for the expression of the BTG-3 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases Bam HI and Asp718. The polyadenylation site of the simian virus (SV)40 is used for efficient polyadenylation. For an easy selection of recombinant viruses the beta-galactosidase gene from *E. coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., *Virology* 170:31–39).

The plasmid is digested with the respective restriction enzymes and dephosphorylated using calf intestinal phosphatase by procedures known in the art. The DNA is then isolated from a 1% agarose gel using the commercially available kit ("GENECLEAN™" BIO 101 Inc., La Jolla, Calif.). This vector DNA is designated V2.

Fragment F2 and the dephosphorylated plasmid V2 are ligated with T4 DNA ligase. *E. coli* HB101 cells are then transformed and bacteria identified that contained the plasmid (pBac BTG-3) with the BTG-3 gene using the enzymes Bam HI and Asp718. The sequence of the cloned fragment is confirmed by DNA sequencing.

5 μg of the plasmid pBac BTG-3 is co-transfected with 1.0 μg of a commercially available linearized baculovirus ("BACULOGOLD™ baculovirus DNA", Pharmingen, San Diego, Calif.) using the lipofection method (Feigner et al., *Proc. Natl. Acad. Sci. (USA)* 84:7413–7417 (1987)).

1 μg of BACULOGOLDT™ virus DNA and 5 μg of the plasmid pBac BTG-3 are mixed in a sterile well of a microtiter plate containing 50 μl of serum free Grace's medium (Life Technologies Inc., Gaithersburg, Md.). Afterwards 10 μl LIPOFECTIN™ plus 90 μl Grace's medium are added, mixed and incubated for 15 minutes at room temperature. Then the transfection mixture is added drop-wise to the Sf9 insect cells (ATCC™ CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with) 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution the viruses are added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-BTG-3 at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labeled proteins visualized by SDS-PAGE and autoradiography.

EXAMPLE 3

Expression of Recombinant BTG-2 in COS Cells

The expression of plasmid, BTG-2 HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire BTG-2 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (Wilson, I. et al., *Cell* 37:767 (1984)). The fusion of HA tag to the target protein allows easy detection of the recombinant protein with an antibody that recognizes the HA epitope.

The plasmid construction strategy is described as follows:

The DNA sequence encoding BTG-2, ATCC™ #97025, is constructed by PCR using two primers: the 5' primer 5' GGCCCAAGCTTGCCGCCATGCAGCT-TGAAATCCAAGTAG 3' (SEQ ID No:9) contains a Hind III site followed by 23 nucleotides of BTG-2 coding sequence starting from the initiation codon; the 3' sequence 5' ATCGTCTAGATTAGTTAGCCATAACAG-GCTGGAATTGCTGGTTAGAATAC TGCATGTTATT-TAAGCTAAAATTCAAGCCATCTA 3' (SEQ ID No:10) contains complementary sequences to XbaI site, translation stop codon, HA tag and the last 68 nucleotides of the BTG-2 coding sequence (not including the stop codon). Therefore, the PCR product contains a Hind III site, BTG-2 coding sequence followed by HA tag fused in frame, a translation termination stop codon next to the HA tag, and an XbaI site. The PCR amplified DNA fragment and the vector, pcDNAI/Amp, are digested with Hind III and XbaI restriction enzyme and ligated. The ligation mixture is transformed into *E. coli* strain SURE (STRATAGENE™ Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant BTG-2, COS cells are transfected with the expression vector by DEAE-DEXTRAN method (Sambrook, J. et al., *Molecular Cloning. A Laboratory Manual*, Cold Spring Harbor Laboratory Press, Cold Spring Harbor, N.Y. (1989)). The expression of the BTG-2 HA protein is detected by radiolabelling and immunoprecipitation method (E. Harlow, D. Lane, Antibodies: A Laboratory Manual, Cold Spring Harbor Laboratory Press, Cold Spring Harbor, N.Y. (1988)). Cells are labeled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). Wilson, I. et al., *Cell* 37:767 (1984)). Both cell lysate and culture media are precipitated with a HA specific monoclonal antibody. Proteins precipitated are analyzed on 15% SDS-PAGE gels.

EXAMPLE 4

Expression of Recombinant BTG-3 in COS Cells

The expression of plasmid, BTG-3 HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire BTG-3 precursor and a HA tag fused in frame to its 3' end is cloned into the polylinker region of the vector, therefore, the recombinant protein expression is directed under the CMV promoter. The HA tag corresponds to an epitope derived from the influenza hemagglutinin protein as previously described (Wilson, I. et al., *Cell* 37:767 (1984)). The infusion of HA tag to the target protein allows easy detection of the recombinant protein with an antibody that recognizes the HA epitope.

The plasmid construction strategy is described as follows:

The DNA sequence encoding BTG-3, ATCC™ #97010, is constructed by PCR using two primers: the 5' primer 5' GGCCCAAGCTTGCCGCC ATGCAGCTAGAGATCAAAGTGGC 3' (SEQ ID No. 11) contains a Hind III site followed by 23 nucleotides of BTG-3 coding sequence starting from the initiation codon; the 3' sequence 5' ATCGTCTAGATCAAGCGTAGTCTGG-GACGTCGTATGGGTAGGTTG TAGCTGAGGCCTTC-CACAAAGGGTGTCTTCTCCAGG 3' (SEQ ID No:12) contains complementary sequences to an XbaI site, translation stop codon, HA tag and the last 68 nucleotides of the BTG-3 coding sequence (not including the stop codon). Therefore, the PCR product contains a Hind III site, BTG-3 coding sequence followed by HA tag fused in frame, a translation termination stop codon next to the HA tag, and an XbaI site. The PCR amplified DNA fragment and the vector, pcDNAI/Amp, are digested with Hind III and XbaI restriction enzymes and ligated. The ligation mixture is transformed into *E. coli* strain SURE (STRATAGENE™ Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant BTG-3, COS cells are transfected with the expression vector by DEAE-DEXTRAN method (Sambrook, J. et al., *Molecular Cloning: A Laboratory Manual*, Cold Spring Laboratory Press, Cold Spring Harbor, N.Y. (1989)). The expression of the BTG-3 HA protein is detected by radiolabelling and immunoprecipitation method (E. Harlow, D. Lane, Antibodies: A Laboratory Manual, Cold Spring Harbor Laboratory Press, Cold Spring Harbor, N.Y. (1988)). Cells are labeled for 8 hours with $^{35}$-cysteine two days post transfection. Culture media is then collected and cells are lysed with detergent (RIPA buffer (150 mM NaCl, 1% NP-40, 0.1% SDS, 1% NP40, 0.5% DOC, 50 mM Tris, pH 7.5) (Wilson, I. et al., *Cell* 37:767 (1984)). Both cell lysate and culture media are precipitated with a HA specific monoclonal antibody. Proteins precipitated are analyzed on 15% SDS-PAGE gels.

EXAMPLE 5

Bacterial Expression and Purification of BTG-2

The DNA sequence encoding BTG-2, ATCC™ #97025, is initially amplified using PCR oligonucleotide primers corresponding to the 5' and 3' end sequences of the processed BTG-2 gene (minus the signal peptide sequence) and the vector sequences 3' to the BTG-2 gene. Additional nucleotides corresponding to NcoI and Bgl II restriction enzyme sites were added to the 5' and 3' end sequences respectively. The 5' oligonucleotide primer has the sequence ATCGC-CATGGGACAGCTTGAAATCCAAGTAGCACTA 3' (SEQ ID No:13) contains a Nco I restriction enzyme site followed by 24 nucleotides of BTG-2 coding sequence. The 3' sequence 5' ATCGAGATCTTTAGTTAGCCATAACAG-GCTGGAAT 3' (SEQ ID No:14) contains complementary sequences to a Bgl II restriction site and the last 21 nucleotides of BTG-2. The restriction enzyme sites correspond to the restriction enzyme sites on the bacterial expression vector pQE-60 (Qiagen, Inc. Chatsworth, Calif.). pQE-60 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-60 is then digested with Nco I and Bgl II. The amplified sequences are ligated into pQE-60 and are inserted in frame with the sequence encoding for the histidine tag and the RBS. The ligation mixture is then used to transform *E. coli* strain M15/rep 4 (Qiagen, Inc.) by the procedure described in Sambrook, J. et al., *Molecular Cloning: A Laboratory Manual,* Cold Spring Harbor Laboratory Press, Cold Spring Harbor, N.Y. (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized BTG-2 is purified from this solution by chromatography on a Nickel-Chelate column under conditions that allow for tight binding by proteins containing the 6-His tag (Hochuli, E. et al., *J Chromatography* 411:177–184 (1984)). BTG-2 (95% pure) is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 6

Bacterial Expression and Purification of BTG-3

The DNA sequence encoding BTG-3, ATCC™ #97010 is initially amplified using PCR oligonucleotide primers corresponding to the 5' and 3' end sequences of the processed BTG-3 gene. Additional nucleotides corresponding to NcoI and Bgl II restriction enzyme sites are added to the 5' and 3' sequences respectively. The 5' oligonucleotide primer has the sequence 5' ATCGCCATGGGACAGCTAGAGAT-CAAAGTGGCCCTG3' (SEQ ID No:15) contains an NcoI restriction enzyme site followed by 24 nucleotides of BTG-3 coding sequence. The 3' sequence 5' ATCGAGATCTGTTG-GCCAGCACCACGGGCTGG 3' (SEQ ID NO.:16) contains complementary sequences to a Bgl II restriction site and the last 21 nucleotides of BTG-3 coding sequence. The restriction enzyme sites correspond to the restriction enzyme sites on the bacterial expression vector pQE-60 (Qiagen, Inc. Chatsworth, Calif.). pQE-60 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-60 is then digested with Nco I and Bgl II. The amplified sequences are ligated into pQE-60 and are inserted in frame with the sequence encoding for the histidine tag and the RBS. The ligation mixture is then used to transform *E. coli* strain M15/rep 4 (Qiagen, Inc.) by the procedure described in Sambrook, J. et al., *Molecular Cloning: A Laboratory Manual,* Cold Spring Harbor Laboratory Press, Cold Spring Harbor, N.Y. (1989) (160860). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 µg/ml) and Kan (25 µg/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized BTG-3 is purified from this solution by chromatography on a Nickel-Chelate column under conditions that allow for tight binding by proteins containing the 6-His tag (Hochuli, E. et al., *J Chromatography* 411:177–184 (16084)). BTG-3 (95% pure) is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 7

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, *DNA* 7:219-25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

It will be clear that the invention may be practiced otherwise than as particularly described in the foregoing description and examples.

Numerous modifications and variations of the present invention are possible in light of the above teachings and, therefore, within the scope of the appended claims, the invention may be practiced otherwise than as particularly described.

The entire disclosure of all publications (including patents, patent applications, journal articles, laboratory manuals, books, or other documents) cited herein are hereby incorporated by reference.

What is claimed is:

1. A method for diagnosing aberrant cellular proliferation associated with a malignant phenotype comprising:
   a) measuring by radioimmunoassay, competitive-binding assay, Western blot analysis, ELISA assay, or sandwich assay the amount of BTG-2 protein in a sample obtained from a patient, using an antibody that specifically binds the amino acid sequence of SEQ ID NO:2; and
   b) comparing the amount of BTG-2 protein to a normal control tissue sample,
wherein under-expression of the BTG-2 protein in the sample obtained from the patient relative to the normal control tissue sample is diagnostic of aberrant cellular proliferation associated with a malignant phenotype, and wherein said BTG-2 protein consists of the amino acid sequence of SEQ ID NO:2, or a fragment thereof.

2. The method of claim 1, wherein said sample obtained from a patient is blood, urine, saliva, tissue biopsy or autopsy material.

3. A method for diagnosing aberrant cellular proliferation associated with a malignant phenotype comprising:
   a) measuring by radioimmunoassay, competitive-binding assay, Western blot analysis, ELISA assay, or sandwich assay the amount of BTG-3 protein in a sample obtained from a patient, using an antibody that specifically binds the amino acid sequence of SEQ ID NO:4; and
   b) comparing the amount of BTG-3 protein to a normal control tissue sample, wherein under-expression of the BTG-3 protein in the sample obtained from the patient relative to the normal control tissue sample is diagnostic of aberrant cellular proliferation associated with a malignant phenotype, and wherein said BTG-3 protein consists of the amino acid sequence of SEQ ID NO:4, or a fragment thereof.

4. The method of claim 3, wherein said sample obtained from a patient is blood, urine, saliva, tissue biopsy or autopsy material.

* * * * *

UNITED STATES PATENT AND TRADEMARK OFFICE
CERTIFICATE OF CORRECTION

| | | |
|---|---|---|
| PATENT NO. | : 7,049,081 B2 | Page 1 of 1 |
| APPLICATION NO. | : 10/739043 | |
| DATED | : May 23, 2006 | |
| INVENTOR(S) | : Kunsch et al. | |

It is certified that error appears in the above-identified patent and that said Letters Patent is hereby corrected as shown below:

Title Page:

On page 1, INID code (56) - "Other Publications", delete "Marshall, C.J., "Tumor suppressor genes," Cell, 86:313-326 (1991)" and insert --Marshall, C.J., "Tumor suppressor genes," Cell, 64:313-326 (1991)--.

In the Claims:

Claim 1, at column 53, delete "or a fragment thereof." and insert --or mature form thereof.--

Claim 3, at column 54, delete "or a fragment thereof." and insert --or mature form thereof.--

Signed and Sealed this

Fifteenth Day of August, 2006

JON W. DUDAS
*Director of the United States Patent and Trademark Office*

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
       (A) LENGTH: 1843 base pairs
       (B) TYPE: nucleic acid
       (C) STRANDEDNESS: double
       (D) TOPOLOGY: linear (ii) MOLECULE TYPE: DNA (genomic)

(ix) FEATURE:
       (A) NAME/KEY: CDS
       (B) LOCATION: 27..1061

(xi) SEQUENCE DESCRIPTION: SEQ ID NO: 1:

```
GGCACGAGAT TTTGTGGCGT AGAGCT ATG CAG CTT GAA ATC CAA GTA GCA CTA         53
                             Met Gln Leu Glu Ile Gln Val Ala Leu
                              1               5

AAT TTT ATT ATT TCG TAT TTG TAC AAT AAG CTT CCC AGG AGA CGT GTC         101
Asn Phe Ile Ile Ser Tyr Leu Tyr Asn Lys Leu Pro Arg Arg Arg Val
 10              15                  20                  25

AAC ATT TTT GGT GAA GAA CTT GAA AGA CTT CTT AAG AAG AAA TAT GAA         149
Asn Ile Phe Gly Glu Glu Leu Glu Arg Leu Leu Lys Lys Lys Tyr Glu
                 30                  35                  40

GGG CAC TGG TAT CCT GAA AAG CCA TAC AAA GGA TCG GGG TTT AGA TGT         197
Gly His Trp Tyr Pro Glu Lys Pro Tyr Lys Gly Ser Gly Phe Arg Cys
                 45                  50                  55

ATA CAC ATA GGG GAG AAA GTG GAC CCA GTG ATT GAA CAA GCA TCC AAA         245
Ile His Ile Gly Glu Lys Val Asp Pro Val Ile Glu Gln Ala Ser Lys
             60                  65                  70

GAG AGT GGT TTG GAC ATT GAT GAT GTT CGT GGC AAT CTG CCA CAG GAT         293
Glu Ser Gly Leu Asp Ile Asp Asp Val Arg Gly Asn Leu Pro Gln Asp
         75                  80                  85

CTT AGT GTT TGG ATC GAC CCA TTT GAG GTT TCT TAC CAA ATT GGT GAA         341
Leu Ser Val Trp Ile Asp Pro Phe Glu Val Ser Tyr Gln Ile Gly Glu
```

```
                     90                  95                 100                 105
AAG GGA CCA GTG AAG GTG CTT TAC GTG GAT GAT AAT AAT GAA AAT GGA                      389
Lys Gly Pro Val Lys Val Leu Tyr Val Asp Asp Asn Asn Glu Asn Gly
                110                 115                 120

TGT GAG TTG GAT AAG GAG ATC AAA AAC AGC TTT AAC CCA GAG GCC CAG                      437
Cys Glu Leu Asp Lys Glu Ile Lys Asn Ser Phe Asn Pro Glu Ala Gln
                125                 130                 135

GTT TTT ATG CCC ATA AGT GAC CCA GCC TCA TCA GTG TCC AGC TCT CCA                      485
Val Phe Met Pro Ile Ser Asp Pro Ala Ser Ser Val Ser Ser Ser Pro
                140                 145                 150

TCG CCT CCT TTT GGT CAC TCT GCT GCT GTA AGC CCT ACC TTC ATG CCC                      533
Ser Pro Pro Phe Gly His Ser Ala Ala Val Ser Pro Thr Phe Met Pro
155                 160                 165

CGG TCC ACT CAG CCT TTA ACC TTT ACC ACT GCC ACT TTT GCT GCC ACC                      581
Arg Ser Thr Gln Pro Leu Thr Phe Thr Thr Ala Thr Phe Ala Ala Thr
170                 175                 180                 185

AAG TTC GGC TCT ACC AAA ATG AAA AAT AGT GGC CGT AGC AAC AAG GTT                      629
Lys Phe Gly Ser Thr Lys Met Lys Asn Ser Gly Arg Ser Asn Lys Val
                190                 195                 200

GCA CGT ACT TCT CCC ATC AAC CTC GGC TTG AAT GTG AAT GAC CTC TTG                      677
Ala Arg Thr Ser Pro Ile Asn Leu Gly Leu Asn Val Asn Asp Leu Leu
                205                 210                 215

AAG CAG AAA GCC ATC TCT TCC TCA ATG CAC TCT CTG TAT GGG CTT GGC                      725
Lys Gln Lys Ala Ile Ser Ser Ser Met His Ser Leu Tyr Gly Leu Gly
                220                 225                 230

TTG GGT AGC CAG CAG CAG CCA CAG CAA CAG CAG CAG CCA GCC CAG CCG                      773
Leu Gly Ser Gln Gln Gln Pro Gln Gln Gln Gln Gln Pro Ala Gln Pro
235                 240                 245

CCA CCG CCA CCA CCA CCA CCA CAG CAG CAA CAA CAG CAG AAA ACC TCT                      821
Pro Pro Pro Pro Pro Pro Pro Gln Gln Gln Gln Gln Gln Lys Thr Ser
250                 255                 260                 265

GCT CTT TCT CCT AAT GCC AAG GAA TTT ATT TTT CCT AAT ATG CAG GGT                      869
Ala Leu Ser Pro Asn Ala Lys Glu Phe Ile Phe Pro Asn Met Gln Gly
                270                 275                 280

CAA GGT AGT AGT ACC AAT GGA ATG TTC CCA GGT GAC AGC CCC CTT AAC                      917
Gln Gly Ser Ser Thr Asn Gly Met Phe Pro Gly Asp Ser Pro Leu Asn
                285                 290                 295

CTC AGT CCT CTC CAG TAC AGT AAT GCC TTT GAT GTG TTT GCA GCC TAT                      965
Leu Ser Pro Leu Gln Tyr Ser Asn Ala Phe Asp Val Phe Ala Ala Tyr
                300                 305                 310

GGA GGC CTC AAT GAG AAG TCT TTT GTA GAT GGC TTG AAT TTT AGC TTA                     1013
Gly Gly Leu Asn Glu Lys Ser Phe Val Asp Gly Leu Asn Phe Ser Leu
315                 320                 325

AAT AAC ATG CAG TAT TCT AAC CAG CAA TTC CAG CCT GTT ATG GCT AAC                     1061
Asn Asn Met Gln Tyr Ser Asn Gln Gln Phe Gln Pro Val Met Ala Asn
330                 335                 340                 345

TAAAAAAAG AAAATGTATC GTACAAGTTA AATGCACGG GCCAAGGGGG GATTTTTT                       1121

TTCACCTCCT TGAGAATTTT TTTTTTTAAG CTTATAGTAA GGATACATTC AAGCTTGG                      1181

AAAAAAATAA TAATAAAACA TGCATCATTT TTCATTTGCC AACCAAGCAC AAAGTTAT                      1241

TATGCTGCCT GTATATTTTA AAGTATACTC TCAGATATGC CCTCTTACAG TATTTTAA                      1301

TATTAGCAAA GGACATGGCT TGATTTTTTT TTATAAAAAT TGGCACTAAT AAGTGGGT                      1361

ATTGGTCTTT TCTAATTGTA TAATTTAATT TAGTACCAAA GTTTGTAAAA TATCAGAG                      1421

TATATATATA TTGTATCCTA CGACATGGTA TTGCATTTAT ATCTTTTTAC TACAGTGA                      1481

TGTGACAGCA GCAGCCTCAT GTTGTATTTT TTTTACTGAA ATTGTAAAAT ATCCATCT                      1541

AAGACATCAA CTATTCTAAA AATTGTGTAC AGGATATTCC TTTAGTGGTG GAATTAAA                      1601
```

```
GTGCGAATAC TTGCTTTCTC CAAAAAAATG TATTTTCTGT TAAAAGTTTA AGATTTT      1661

CTATATATTA TGGAAGGAAA ATGTAATCGT AAATATTAAT TTTGTACCTA TATTGTGC    1721

TACTTGAAAA AAACGGTATA AAAGTATTTT GAGTCAGTGT CTTACATGTT AAGAGGGA    1781

GAAATAGTTT ATATTAAGTT TGTATTAAAA TTCTTTAAAA TTAAAAAAAA AAAAAAA    1841

AA                                                                 1843
```

(2) INFORMATION FOR SEQ ID NO: 2:

(i) SEQUENCE CHARACTERISTICS:
        (A) LENGTH: 345 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Gln Leu Glu Ile Gln Val Ala Leu Asn Phe Ile Ile Ser Tyr Leu
 1               5                  10                  15

Tyr Asn Lys Leu Pro Arg Arg Val Asn Ile Phe Gly Glu Glu Leu
            20                  25                  30

Glu Arg Leu Leu Lys Lys Lys Tyr Glu Gly His Trp Tyr Pro Glu Lys
        35                  40                  45

Pro Tyr Lys Gly Ser Gly Phe Arg Cys Ile His Ile Gly Glu Lys Val
    50                  55                  60

Asp Pro Val Ile Glu Gln Ala Ser Lys Glu Ser Gly Leu Asp Ile Asp
 65                  70                  75                  80

Asp Val Arg Gly Asn Leu Pro Gln Asp Leu Ser Val Trp Ile Asp Pro
                85                  90                  95

Phe Glu Val Ser Tyr Gln Ile Gly Glu Lys Gly Pro Val Lys Val Leu
            100                 105                 110

Tyr Val Asp Asp Asn Asn Glu Asn Gly Cys Glu Leu Asp Lys Glu Ile
        115                 120                 125

Lys Asn Ser Phe Asn Pro Glu Ala Gln Val Phe Met Pro Ile Ser Asp
    130                 135                 140

Pro Ala Ser Ser Val Ser Ser Pro Ser Pro Phe Gly His Ser
145                 150                 155                 160

Ala Ala Val Ser Pro Thr Phe Met Pro Arg Ser Thr Gln Pro Leu Thr
                165                 170                 175

Phe Thr Thr Ala Thr Phe Ala Ala Thr Lys Phe Gly Ser Thr Lys Met
            180                 185                 190

Lys Asn Ser Gly Arg Ser Asn Lys Val Ala Arg Thr Ser Pro Ile Asn
        195                 200                 205

Leu Gly Leu Asn Val Asn Asp Leu Leu Lys Gln Lys Ala Ile Ser Ser
    210                 215                 220

Ser Met His Ser Leu Tyr Gly Leu Gly Leu Gly Ser Gln Gln Gln Pro
225                 230                 235                 240

Gln Gln Gln Gln Gln Pro Ala Gln Pro Pro Pro Pro Pro Pro
                245                 250                 255

Gln Gln Gln Gln Gln Gln Lys Thr Ser Ala Leu Ser Pro Asn Ala Lys
            260                 265                 270

Glu Phe Ile Phe Pro Asn Met Gln Gly Gln Gly Ser Ser Thr Asn Gly
        275                 280                 285

Met Phe Pro Gly Asp Ser Pro Leu Asn Leu Ser Pro Leu Gln Tyr Ser
    290                 295                 300
```

```
Asn Ala Phe Asp Val Phe Ala Ala Tyr Gly Gly Leu Asn Glu Lys Ser
305                 310                 315                 320

Phe Val Asp Gly Leu Asn Phe Ser Leu Asn Asn Met Gln Tyr Ser Asn
                325                 330                 335

Gln Gln Phe Gln Pro Val Met Ala Asn
            340                 345

(2) INFORMATION FOR SEQ ID NO: 3:

(i) SEQUENCE CHARACTERISTICS:
        (A) LENGTH: 1343 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 229..1260

(xi) SEQUENCE DESCRIPTION: SEQ ID NO: 3:
```

| | |
|---|---|
| GGAATTCGGC ACGAGCAACC CTCAACGACG AAAAGGACTT CGGTCCCCTG GCCCGGCGAC | 60 |
| GCCCGGGAAG GAAAGGAGAG CGACCTCCGC CCCGCGCTCA GGCCACCCTG GAGGGAGAA | 120 |
| CCGCCCCGCG CSSGSGTTAG AGCGCCCCGC CGCCCCGTAG ACCCGAAGCC GCCTGGAGC | 180 |

```
CAAGGCTGTA CACGTGCCCT GTGCTGATTC TCTGCCTAGG AAAGGACC ATG CAG CTA        237
                                                    Met Gln Leu
                                                      1

GAG ATC AAA GTG GCC CTG AAC TTC ATC ATC TCC TAC TTG TAC AAC AAG         285
Glu Ile Lys Val Ala Leu Asn Phe Ile Ile Ser Tyr Leu Tyr Asn Lys
      5                  10                  15

CTG CCC CGG CGC CGG GCA GAC CTG TTT GGG GAG GAG CTA GAG CGG CTT         333
Leu Pro Arg Arg Arg Ala Asp Leu Phe Gly Glu Glu Leu Glu Arg Leu
 20                  25                  30                  35

TTG AAA AGG AAA TAT GAA GGC CAC TGG TAC CCT GAG AAG CCA CTG AAA         381
Leu Lys Arg Lys Tyr Glu Gly His Trp Tyr Pro Glu Lys Pro Leu Lys
         40                  45                  50

GGC TCT GGC TTC CGC TGT GTT CAC ATT GGG GAG ATG GTG GAC CCC GTG         429
Gly Ser Gly Phe Arg Cys Val His Ile Gly Glu Met Val Asp Pro Val
             55                  60                  65

GTG GAG CTG GCC GCC AAG CGG AGT GGC CTG GCG GTG GAA GAT GTG CGG         477
Val Glu Leu Ala Ala Lys Arg Ser Gly Leu Ala Val Glu Asp Val Arg
 70                  75                  80

GCC AAT GTG CCT GAG GAG CTG AGT GTC TGG ATT GAT CCC TTT GAG GTG         525
Ala Asn Val Pro Glu Glu Leu Ser Val Trp Ile Asp Pro Phe Glu Val
         85                  90                  95

TCC TAC CAG ATT GGT GAG AAG GGA GCT GTG AAA GTG CTG TAC CTG GAT         573
Ser Tyr Gln Ile Gly Glu Lys Gly Ala Val Lys Val Leu Tyr Leu Asp
100                 105                 110                 115

GAC AGT GAG GGT TGC GGT GCC CCA GAG CTG GAC AAG GAG ATC AAG AGC         621
Asp Ser Glu Gly Cys Gly Ala Pro Glu Leu Asp Lys Glu Ile Lys Ser
                120                 125                 130

AGC TTC AAC CCT GAC GCC CAG GTG TTC GTG CCC ATT GGC AGC CAG GAC         669
Ser Phe Asn Pro Asp Ala Gln Val Phe Val Pro Ile Gly Ser Gln Asp
            135                 140                 145

AGC TCC CTG TCC AAC TCC CCA TCG CCA TCC TTT GGC CAG TCA CCC AGC         717
Ser Ser Leu Ser Asn Ser Pro Ser Pro Ser Phe Gly Gln Ser Pro Ser
        150                 155                 160

CCT ACC TTC ATT CCC CGC TCC GCT CAG CCC ATC ACC TTC ACC ACC GCC         765
Pro Thr Phe Ile Pro Arg Ser Ala Gln Pro Ile Thr Phe Thr Thr Ala
```

-continued

```
                165                 170                 175
TCC TTC GCT GCC ACC AAA TTT GGC TCC ACT AAG ATG AAG AAG GGG GGC    813
Ser Phe Ala Ala Thr Lys Phe Gly Ser Thr Lys Met Lys Lys Gly Gly
180                 185                 190                 195

GGG GCA GCA AGT GGT GGG GGT GTA GCC AGC AGT GGG GCG GGT GGC CAG    861
Gly Ala Ala Ser Gly Gly Gly Val Ala Ser Ser Gly Ala Gly Gly Gln
                200                 205                 210

CAG CCA CCA CAG CAG CCT CGC ATG GCC CGC TCA CCC ACC AAC AGC CTG    909
Gln Pro Pro Gln Gln Pro Arg Met Ala Arg Ser Pro Thr Asn Ser Leu
            215                 220                 225

CTG AAG CAC AAG AGC CTC TCT CTG TCT ATG CAT TCA CTG AAC TTC ATC    957
Leu Lys His Lys Ser Leu Ser Leu Ser Met His Ser Leu Asn Phe Ile
        230                 235                 240

ACG GCC AAC CCG GCC CCT CAG TCC CAG CTC TCA CCC AAT GCC AAG GAG   1005
Thr Ala Asn Pro Ala Pro Gln Ser Gln Leu Ser Pro Asn Ala Lys Glu
    245                 250                 255

TTC GTG TAC AAC GGT GGT GGC TCA CCC AGC CTC TTC TTT GAT GCG GCC   1053
Phe Val Tyr Asn Gly Gly Gly Ser Pro Ser Leu Phe Phe Asp Ala Ala
260                 265                 270                 275

GAT GGC CAG GGC AGC GGC ACC CCA GGC CCG TTT GGA GGC AGT GGG GCT   1101
Asp Gly Gln Gly Ser Gly Thr Pro Gly Pro Phe Gly Gly Ser Gly Ala
                280                 285                 290

GGC ACC TGC AAC AGC AGC AGC TTT GAC ATG GCC CAG GTA TTT GGA GGT   1149
Gly Thr Cys Asn Ser Ser Ser Phe Asp Met Ala Gln Val Phe Gly Gly
            295                 300                 305

GGT GCC AAC AGC CTC TTC CTG GAG AAG ACA CCC TTT GTG GAA GGC CTC   1197
Gly Ala Asn Ser Leu Phe Leu Glu Lys Thr Pro Phe Val Glu Gly Leu
        310                 315                 320

AGC TAC AAC CTG AAC ACC ATG CAG TAT CCC AGC CAG CAG TTC CAG CCC   1245
Ser Tyr Asn Leu Asn Thr Met Gln Tyr Pro Ser Gln Gln Phe Gln Pro
    325                 330                 335

GTG GTG CTG GCC AAC TGACCATCTA CCTGGCCCGT GGGGGCAGGA GCACCCAAGA   1300
Val Val Leu Ala Asn
340

CCACAGAAAA GAGAAAGGAA AGGCCAAAAA AAAAAAAAAA AAA                   1343
```

(2) INFORMATION FOR SEQ ID NO: 4:

(i) SEQUENCE CHARACTERISTICS:
        (A) LENGTH: 344 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Gln Leu Glu Ile Lys Val Ala Leu Asn Phe Ile Ile Ser Tyr Leu
1               5                   10                  15

Tyr Asn Lys Leu Pro Arg Arg Ala Asp Leu Phe Gly Glu Glu Leu
            20                  25                  30

Glu Arg Leu Leu Lys Arg Lys Tyr Glu Gly His Trp Tyr Pro Glu Lys
        35                  40                  45

Pro Leu Lys Gly Ser Gly Phe Arg Cys Val His Ile Gly Glu Met Val
    50                  55                  60

Asp Pro Val Val Glu Leu Ala Ala Lys Arg Ser Gly Leu Ala Val Glu
65                  70                  75                  80

Asp Val Arg Ala Asn Val Pro Glu Glu Leu Ser Val Trp Ile Asp Pro
                85                  90                  95

Phe Glu Val Ser Tyr Gln Ile Gly Glu Lys Gly Ala Val Lys Val Leu
```

-continued

```
                     100                 105                 110
    Tyr Leu Asp Asp Ser Glu Gly Cys Gly Ala Pro Glu Leu Asp Lys Glu
                 115                 120                 125

Ile Lys Ser Ser Phe Asn Pro Asp Ala Gln Val Phe Val Pro Ile Gly
                 130                 135                 140

Ser Gln Asp Ser Ser Leu Ser Asn Ser Pro Ser Pro Ser Phe Gly Gln
    145                 150                 155                 160

Ser Pro Ser Pro Thr Phe Ile Pro Arg Ser Ala Gln Pro Ile Thr Phe
                     165                 170                 175

Thr Thr Ala Ser Phe Ala Ala Thr Lys Phe Gly Ser Thr Lys Met Lys
                 180                 185                 190

Lys Gly Gly Gly Ala Ala Ser Gly Gly Val Ala Ser Ser Gly Ala
                 195                 200                 205

Gly Gly Gln Gln Pro Pro Gln Gln Pro Arg Met Ala Arg Ser Pro Thr
                 210                 215                 220

Asn Ser Leu Leu Lys His Lys Ser Leu Ser Leu Ser Met His Ser Leu
    225                 230                 235                 240

Asn Phe Ile Thr Ala Asn Pro Ala Pro Gln Ser Gln Leu Ser Pro Asn
                     245                 250                 255

Ala Lys Glu Phe Val Tyr Asn Gly Gly Ser Pro Ser Leu Phe Phe
                 260                 265                 270

Asp Ala Ala Asp Gly Gln Gly Ser Gly Thr Pro Gly Pro Phe Gly Gly
                 275                 280                 285

Ser Gly Ala Gly Thr Cys Asn Ser Ser Ser Phe Asp Met Ala Gln Val
                 290                 295                 300

Phe Gly Gly Gly Ala Asn Ser Leu Phe Leu Glu Lys Thr Pro Phe Val
    305                 310                 315                 320

Glu Gly Leu Ser Tyr Asn Leu Asn Thr Met Gln Tyr Pro Ser Gln Gln
                     325                 330                 335

Phe Gln Pro Val Val Leu Ala Asn
                 340
```

(2) INFORMATION FOR SEQ ID NO: 5:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

CAGTGGATCC GCCACCATGC AGCTTGAAAT CCAAGTAGCA C         41

(2) INFORMATION FOR SEQ ID NO: 6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

CAGTGGTACC ATACATTTTC TTTTTTTTAG TTAGCCAT         38

(2) INFORMATION FOR SEQ ID NO: 7:

(i) SEQUENCE CHARACTERISTICS:
    (A) LENGTH: 41 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 7:

CAGTGGATCC GCCACCATGC AGCTAGAGAT CAAAGTGGCC C                41

(2) INFORMATION FOR SEQ ID NO: 8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

CAGTGGTACC ACGGGCCAGG TAGATGGTCA GTTGGCCAGC AC               42

(2) INFORMATION FOR SEQ ID NO: 9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GGCCCAAGCT TGCCGCCATG CAGCTTGAAA TCCAAGTAG                   39

(2) INFORMATION FOR SEQ ID NO: 10:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

ATCGTCTAGA TTAGTTAGCC ATAACAGGCT GGAATTGCTG GTTAGAATAC TGCATGTTAT      60

TTAAGCTAAA ATTCAAGCCA TCTA                                            84

(2) INFORMATION FOR SEQ ID NO: 11:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1    1:

GGCCCAAGCT TGCCGCCATG CAGCTAGAGA TCAAAGTGGC                  40

(2) INFORMATION FOR SEQ ID NO: 12:

(i) SEQUENCE CHARACTERISTICS:

(A) LENGTH: 81 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1   2:

ATCGTCTAGA TCAAGCGTAG TCTGGGACGT CGTATGGGTA GGTTGTAGCT GAGGCCTTCC      60

ACAAAGGGTG TCTTCTCCAG G                                                81

(2) INFORMATION FOR SEQ ID NO: 13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

ATCGCCATGG GACAGCTTGA AATCCAAGTA GCACTA                                36

(2) INFORMATION FOR SEQ ID NO: 14:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cD    NA (xi) SEQUENCE DESCRIPTION: SEQ ID NO: 14:

ATCGAGATCT TTAGTTAGCC ATAACAGGCT GGAAT                                 35

(2) INFORMATION FOR SEQ ID NO: 15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cD    NA (xi) SEQUENCE DESCRIPTION: SEQ ID NO: 15:

ATCGCCATGG GACAGCTAGA GATCAAAGTG GCCCTG                                36

(2) INFORMATION FOR SEQ ID NO: 16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

ATCGAGATCT GTTGGCCAGC ACCACGGGCT GG                                    32

(2) INFORMATION FOR SEQ ID NO: 17:

(i) SEQUENCE CHARACTERISTICS:
        (A) LENGTH: 171 amino acids
        (B) TYPE: amino acid -continued (C) STRANDEDNESS: not relevant
    (D) TOPOLOGY: linear (ii) MOLECULE TYPE: protein (xi) SEQUENCE DESCRIPTION: SEQ ID NO: 17:

Met His Pro Phe Tyr Thr Arg Ala Ala Thr Met Ile Gly Glu Ile Al
1               5                  10                  15

Ala Ala Val Ser Phe Ile Ser Lys Phe Leu Arg Thr Lys Gly Leu Th
            20                  25                  30

Ser Glu Arg Gln Leu Gln Thr Phe Ser Gln Ser Leu Gln Glu Leu Le
        35                  40                  45

Ala Glu His Tyr Lys His His Trp Phe Pro Glu Lys Pro Cys Lys Gl
    50                  55                  60

Ser Gly Tyr Arg Cys Ile Arg Ile Asn His Lys Met Asp Pro Leu Il
65                  70                  75                  80

Gly Gln Ala Ala Gln Arg Ile Gly Leu Ser Ser Gln Glu Leu Phe Ar
                85                  90                  95

Leu Leu Pro Ser Glu Leu Thr Leu Trp Val Asp Pro Tyr Glu Val Se
            100                 105                 110

Tyr Arg Ile Gly Glu Asp Gly Ser Ile Cys Val Leu Tyr Glu Ala Se
        115                 120                 125

Pro Ala Gly Gly Ser Thr Gln Asn Ser Thr Asn Val Gln Met Val As
    130                 135                 140

Ser Arg Ile Ser Cys Lys Glu Glu Leu Leu Leu Gly Arg Thr Ser Pr
145                 150                 155                 160

Ser Lys Asn Tyr Asn Met Met Thr Val Ser Gly
                165                 170

(2) INFORMATION FOR SEQ ID NO: 18:

(i) SEQUENCE CHARACTERISTICS:
        (A) LENGTH: 213 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 18:

Met Gln Leu Glu Ile Val Ala Leu Asn Phe Ile Ile Ser Tyr Leu Ty
1               5                  10                  15

Asn Lys Leu Pro Arg Arg Arg Phe Gly Glu Glu Leu Glu Arg Leu Le
            20                  25                  30

Lys Lys Tyr Glu Gly His Trp Tyr Pro Glu Lys Pro Lys Gly Ser Gl
        35                  40                  45

Phe Arg Cys Ile His Ile Gly Glu Lys Val Asp Pro Val Ile Glu Gl
    50                  55                  60

Ala Ala Lys Arg Ser Gly Leu Asp Val Arg Asn Leu Pro Glu Leu Se
65                  70                  75                  80

Val Trp Ile Asp Pro Phe Glu Val Ser Tyr Gln Ile Gly Glu Lys Gl
                85                  90                  95

Val Lys Val Leu Tyr Asp Asp Gly Glu Leu Asp Lys Glu Ile Leu Ly
            100                 105                 110

Ser Ser Phe Asn Pro Ala Gln Val Phe Pro Ile Ser Ser Ser Ser Pr
        115                 120                 125

Ser Pro Phe Gly Ser Ser Pro Thr Phe Pro Arg Ser Gln Pro Thr Ph
    130                 135                 140

```
Thr Thr Ala Phe Ala Ala Thr Lys Phe Gly Ser Thr Lys Met Lys Gl
145                 150                 155                 160

Gly Asn Leu Leu Lys Lys Ser Ser Met His Ser Leu Gln Gln Leu Se
                165                 170                 175

Pro Asn Ala Lys Glu Phe Phe Gly Gln Gly Ser Thr Gly Phe Gly As
                180             185                 190

Ser Phe Ala Leu Phe Val Gly Leu Leu Asn Met Gln Tyr Gln Gln Ph
            195                 200             205

Gln Pro Val Ala Asn
        210
```